United States Patent
Saito et al.

(10) Patent No.: US 9,918,613 B2
(45) Date of Patent: Mar. 20, 2018

(54) ENDOSCOPE SYSTEM AND OPERATING METHOD THEREOF

(71) Applicant: FUJIFILM Corporation, Tokyo (JP)

(72) Inventors: Takaaki Saito, Ashigarakami-gun (JP); Hiroshi Yamaguchi, Ashigarakami-gun (JP); Takayuki Iida, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 439 days.

(21) Appl. No.: 14/172,729

(22) Filed: Feb. 4, 2014

(65) Prior Publication Data

US 2014/0152790 A1 Jun. 5, 2014

Related U.S. Application Data

(63) Continuation of application No. PCT/JP2012/071173, filed on Aug. 22, 2012.

(30) Foreign Application Priority Data

Sep. 5, 2011 (JP) .................... 2011-193185

(51) Int. Cl.
*A61B 1/00* (2006.01)
*G06T 5/00* (2006.01)
(Continued)

(52) U.S. Cl.
CPC ........ *A61B 1/00045* (2013.01); *A61B 1/0005* (2013.01); *A61B 1/00009* (2013.01);
(Continued)

(58) Field of Classification Search
CPC . A61B 1/00045; A61B 1/0005; A61B 1/0638; A61B 5/14551; A61B 5/1459; A61B 1/00; G06T 5/008; G06T 5/00
(Continued)

(56) References Cited

U.S. PATENT DOCUMENTS 5,187,572 A 2/1993 Nakamura et al.
5,550,582 A 8/1996 Takasugi et al.
(Continued)

FOREIGN PATENT DOCUMENTS

JP 5-56918 A 3/1993
JP 5-84218 A 4/1993
(Continued)

OTHER PUBLICATIONS

International Search Report, issued in PCT/JP2012/071173, dated Oct. 23, 2012.
(Continued)

*Primary Examiner* — Tung Vo
*Assistant Examiner* — Zaihan Jiang
(74) *Attorney, Agent, or Firm* — Birch, Stewart, Kolasch & Birch, LLP

(57) ABSTRACT

An observation object is imaged under irradiation with oxygen saturation level measurement light to obtain a first image signal, and the observation object is imaged under irradiation with white light to obtain a second image signal. A normal light image is produced from the second image signal. An oxygen saturation level is calculated from the first and second image signals. The calculated oxygen saturation level is imaged in an oxygen saturation image. By superimposing the normal light image on the oxygen saturation image, an emphasized oxygen saturation image is produced. In the emphasized oxygen saturation image, an abnormal area in which a calculation result of the oxygen saturation level is likely to be abnormal is emphasized by its brightness. The produced emphasized oxygen saturation image is displayed on a display device.

9 Claims, 18 Drawing Sheets

(51) Int. Cl.
*A61B 1/06* (2006.01)
*A61B 5/1455* (2006.01)
*A61B 5/1459* (2006.01)
*G06T 7/00* (2017.01)
*A61B 5/00* (2006.01)

(52) U.S. Cl.
CPC ......... *A61B 1/0638* (2013.01); *A61B 1/0653* (2013.01); *A61B 5/1459* (2013.01); *A61B 5/14551* (2013.01); *G06T 5/008* (2013.01); *G06T 7/0012* (2013.01); *A61B 1/063* (2013.01); *A61B 5/489* (2013.01); *G06T 2207/10016* (2013.01); *G06T 2207/10024* (2013.01); *G06T 2207/10068* (2013.01); *G06T 2207/10152* (2013.01); *G06T 2207/20221* (2013.01); *G06T 2207/30028* (2013.01)

(58) Field of Classification Search
USPC ...................................................... 348/68, 65
See application file for complete search history.

(56) References Cited

U.S. PATENT DOCUMENTS

| | | | |
|---|---|---|---|
| 5,956,416 | A | 9/1999 | Tsuruoka et al. |
| 2003/0236458 | A1* | 12/2003 | Hochman ............ A61B 5/0059 600/431 |
| 2006/0241456 | A1* | 10/2006 | Karasawa ............. A61B 8/463 600/447 |
| 2008/0051648 | A1* | 2/2008 | Suri ....................... A61B 6/481 600/407 |
| 2011/0122241 | A1* | 5/2011 | Wang ..................... G06T 5/008 348/65 |
| 2011/0237882 | A1* | 9/2011 | Saito .................. A61B 1/00009 600/109 |
| 2011/0301447 | A1* | 12/2011 | Park ...................... G06T 7/0016 600/407 |
| 2011/0311133 | A1* | 12/2011 | Hirota ................... G06T 7/0012 382/164 |

FOREIGN PATENT DOCUMENTS

| | | |
|---|---|---|
| JP | 6-335451 A | 12/1994 |
| JP | 2648494 B2 | 8/1997 |
| JP | 3-80834 A | 6/1998 |
| JP | 2768936 B2 | 6/1998 |
| JP | 10-210324 A | 8/1998 |
| JP | 2003-284682 A | 10/2003 |

OTHER PUBLICATIONS

Written Opinion of the International Searching Authority, issued in PCT/JP2012/071173, dated Oct. 23, 2012.
Forms PCT/IB/338, PCT/IB/373 and PCT/ISA/237 dated Mar. 20, 2014 for International Application No. PCT/JP2012/071173.
Extended European Search Report, dated Apr. 23, 2015, for European Patent Application No. 12829972.4.
Chinese Office Action and Search Report, dated Jul. 30, 2015, for Chinese Application No. 201280043178.3, together with a partial English translation thereof.
Japanese Office Action, dated Sep. 2, 2015, for Japanese Application No. 2013-532529, together with an English translation thereof.
Chinese Office Action, dated Oct. 18, 2016, for Chinese Patent Application No. 201280043178.3.
Chinese Office Action, dated Apr. 18, 2016, for Chinese Patent Application No. 201280043178.3.

* cited by examiner

ENDOSCOPE SYSTEM AND OPERATING METHOD THEREOF

CROSS REFERENCE TO RELATED APPLICATIONS

This application is a Bypass Continuation of PCT International Application No. PCT/JP2012/071173 filed on Aug. 22, 2012, which claims priority under 35 U.S.C § 119(a) to Patent Application No. 2011-193185 filed in Japan on Sep. 5, 2011, all of which are hereby expressly incorporated by reference into the present application.

BACKGROUND OF THE INVENTION

1. Field of the Invention

The present invention relates to an endoscope system for producing a biological function information image, which images biological function information including the amount of hemoglobin in blood, an oxygen saturation level, and the like, and an operating method thereof.

2. Description Related to the Prior Art

In recent medical care, an endoscope system that is provided with a light source device, an endoscope device, and a processor device is widely used. In an endoscopic diagnosis using this endoscope system, not only normal light observation that uses white light being broad band light as illumination light, but also special light observation that emphasizes a blood vessel of an observation object in display by using narrow band light in a narrowed wavelength band has become widespread.

Besides the special light observation, it is performed to calculate biological function information, including the amount of hemoglobin, an oxygen saturation level, and the depth of a blood vessel, from an image signal obtained by the endoscope system with the use of a light absorption property of the blood vessel and a scattering property of living body tissue, and image the calculated biological function information. For example, a pseudo color oxygen saturation image, which is colored in accordance with the magnitude of the oxygen saturation level, is produced in Japanese Patent No. 2648494. This oxygen saturation image facilitates finding out a cancer being in a hypoxic state.

Since the biological function information is obtained by an arithmetic process based on the image signal, the correctness of the oxygen saturation level itself is reduced unless the image signal is obtained in an appropriate imaging condition. For example, when a pixel value of the image signal is abnormally high because of too high intensity of the illumination light applied to the observation object, the correctness of the oxygen saturation level obtained from that image signal is regarded to be low.

Against this problem, according to Japanese Patent No. 2768936 and U.S. Pat. No. 5,956,416 corresponding to Japanese Patent No. 3217343, an area in which the pixel value of the image signal is beyond a certain threshold value is detected as an abnormal area, and processing and control for differing display of this abnormal area from that of a normal area in which the pixel value is not beyond the threshold value (for example, by masking) are performed. This allows a user to easily distinguish an incorrect area from an area having the correct biological function information such as the oxygen saturation level.

According to the method of distinguishing the abnormal area from the normal area using the certain threshold value as a border, as described in the Japanese Patent No. 2768936 and the U.S. Pat. No. 5,956,416, if the pixel value of the abnormal area largely exceeds the threshold value, in other words, in the case of the occurrence of halation, the reliability of the oxygen saturation level is precisely reflected in display of the abnormal area on a screen. However, although an area is judged to be the abnormal area, if the pixel value of the abnormal area is just slightly above the threshold value and the actual reliability of the oxygen saturation level is not low, the reliability of the oxygen saturation level is not precisely reflected in display of the abnormal area on the screen. On the contrary, although an area is judged to be the normal area, if the pixel value of the normal area is just slightly below the threshold value and the actual reliability of the oxygen saturation level is low, the reliability of the oxygen saturation level is not precisely reflected in display of the normal area on the screen. Therefore, there is a demand for an endoscope system that can precisely display the reliability of the biological function information such as the oxygen saturation level.

SUMMARY OF THE INVENTION

The present invention aims to provide an endoscope system and an operating method thereof that can precisely display the reliability of the biological function information such as the oxygen saturation level.

To achieve the above object, an endoscope system according to the present invention includes an image information obtaining section, a biological function information calculating section, a first image generating section, an emphasized image generating section, and a display section. The image information obtaining section obtains image information by imaging an observation object. The biological function information calculating section calculates biological function information of the observation object based on the image information. The first image generating section produces a biological function information image that images the biological function information. The emphasized image generating section produces an emphasized image. In the emphasized image, a bright part within an abnormal area in which a calculation result of the biological function information calculating section is likely to be abnormal in the biological function information image is further brightened for emphasis. The display section displays the emphasized image.

It is preferable that the endoscope system further includes a second image generating section for producing based on the image information a normal light image that images the observation object irradiated with white light. The emphasized image generating section preferably produces the emphasized image by superimposing the biological function information image on the normal light image.

The biological function information image is preferably composed of luminance information and color difference information. It is preferable that the emphasized image generating section applies no information process to the color difference information of the biological function information image, and applies an information process to the luminance information of the biological function information image so as to further brighten a bright part. The emphasized image generating section preferably adjusts a pixel value of the biological function information image so as to further brighten the bright part.

It is preferable that the endoscope system further includes a halation detecting section and a display control section. The halation detecting section detects whether or not a halation area exists in the biological function information image. In the halation area, a pixel value exceeds a halation value being a certain value or more. In a case where the halation area is detected, the display control section displays the biological function information image on the display section. In a case where no halation area is detected, the display control section displays the emphasized image on the display section.

The biological function information preferably includes a blood volume being the amount of hemoglobin in blood and an oxygen saturation level of the hemoglobin in the blood. The biological function information calculating section preferably isolates information on the blood volume and information on the oxygen saturation level from a plurality of types of the biological function information included in the image information.

The image information preferably includes first image information and second image information. The first image information is obtained by imaging the observation object under irradiation with first illumination light having a first wavelength range in which a light absorption coefficient varies with a variation in the oxygen saturation level. The second image information is obtained by imaging the observation object under irradiation with second illumination light having a second wavelength range different from the first wavelength range.

An operating method of an endoscope system according to the present invention includes the steps of obtaining image information by an image information obtaining section by imaging an observation object; calculating biological function information of the observation object based on the image information by a biological function information calculating section; producing by a first image generating section a biological function information image that images the biological function information; producing an emphasized image by an emphasized image generating section, in said emphasized image, a bright part within an abnormal area in which a calculation result of the biological function information calculating section is likely to be abnormal in the biological function information image being further brightened for emphasis; and displaying the emphasized image on a display section.

According to the present invention, the emphasized image, in which the bright part of the abnormal area in which the calculation result of the biological function information calculating section is likely to be abnormal is further brightened for emphasis, is displayed on the display section. The abnormal area is displayed in the emphasized image so as to be just emphasized by the brightness to facilitate a grasp at sight, instead of determining a border with a normal area using a threshold value just as in the case of the Japanese Patent No. 2768936 and the U.S. Pat. No. 5,956,416. Therefore, it is possible to indicate the reliability of the biological function information, including the oxygen saturation level and the like, with high precision.

Note that, as for the biological function information image having the halation area that already exists, it is apparent that the calculation result of the halation area is abnormal. Thus, in the present invention, the biological function information image having the halation area is displayed on the display section as is, without producing the emphasized image. This eliminates time required for producing the emphasized image and improves the property of a moving image.

BRIEF DESCRIPTION OF DRAWINGS

For more complete understanding of the present invention, and the advantage thereof, reference is now made to the subsequent descriptions taken in conjunction with the accompanying drawings, in which.

DESCRIPTION OF THE PREFERRED EMBODIMENTS

Figure 1:
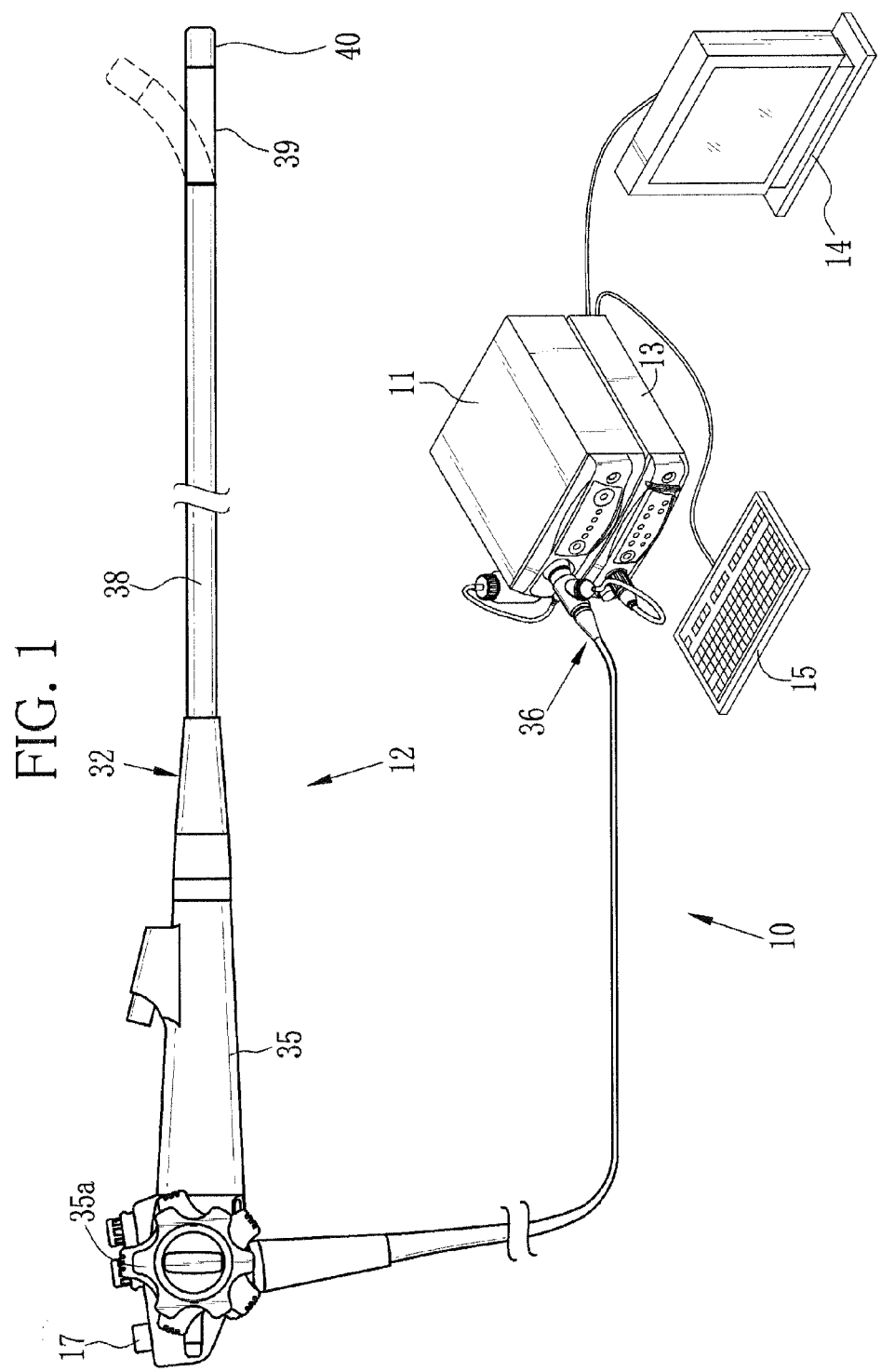
FIG. 1 is a schematic view of an endoscope system.
Figure 2:
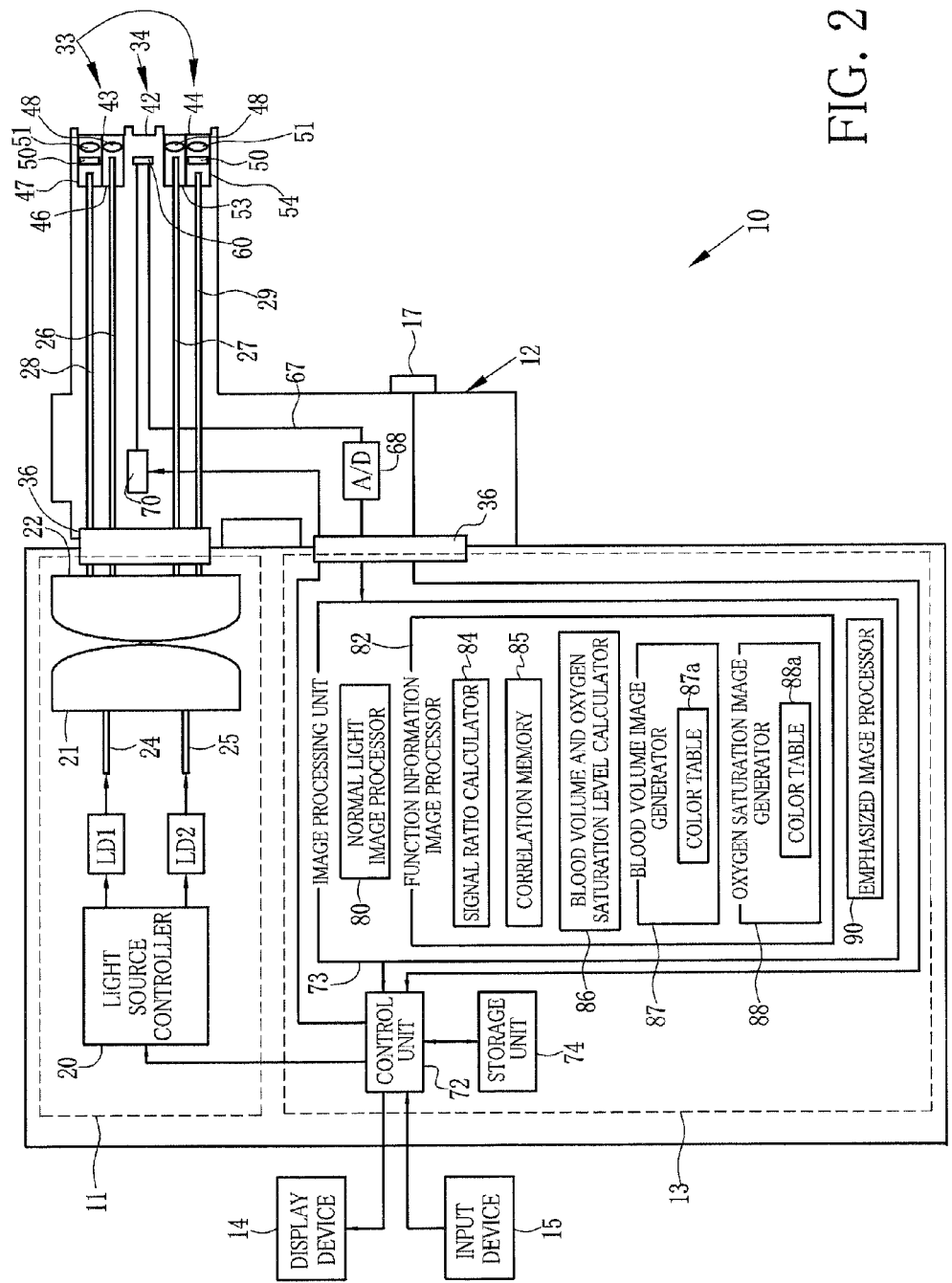
FIG. 2 is a block diagram showing the internal structure of the endoscope system.

As shown in FIGS. 1 and 2, an endoscope system 10 according to a first embodiment is provided with a light source device 11 for emitting light in a predetermined wavelength band, an endoscope system 12 for imaging an area to be observed of an observation object while illuminating the observation object with the light from the light source device 11, a processor device 13 for processing an image signal obtained by the endoscope device 12, a display device 14 for displaying an image of the observation object based on the image signal processed by the processor device 13, and an input device 15 including a keyboard for inputting various types of information to the processor device 13 and the like.

The endoscope system 10 has a normal observation mode and a biological information observation mode. In the normal observation mode, a normal light image, being an image of the observation object under visible light whose wavelength range extends from blue to red, is displayed on the display device 14. In the biological information observation mode, a blood volume image, which images the amount of hemoglobin in blood in the observation object, and an oxygen saturation image, which images an oxygen saturation level of hemoglobin, are displayed on the display device 14. The endoscope system 10 is switched between the observation modes by operation of a switch 17 of the endoscope device 12 or the input device 15.

The light source device 11 is provided with two types of laser light sources LD1 and LD2, a light source controller 20, a combiner 21, and a coupler 22. The laser light source LD1 emits narrow band light (oxygen saturation level measurement light) used for measuring an oxygen saturation level. The laser light source LD2 emits excitation light for exciting a phosphor 50 disposed at a distal end portion of the endoscope device 12. Fluorescence emitted from the excited phosphor 50 and the excitation light produce white light. The light emitted from the laser light sources LD1 and LD2 enter optical fibers 24 and 25 through condenser lenses (not shown), respectively. Note that, as the laser light sources LD1 and LD2, a broad-area type InGaN laser diode, InGaNAs laser diode, GaNAs laser diode, or the like is available.

The light source controller 20 controls the laser light sources LD1 and LD2 so as to adjust emission timing of each laser source and a light amount ratio between the laser sources LD1 and LD2. In this embodiment, in the normal observation mode, the laser light source LD1 is turned off, while the laser light source LD2 is turned on. In the biological information observation mode, on the other hand, the laser light sources LD1 and LD2 are turned on and off alternately.

The combiner 21 combines light from the optical fibers 24 and 25. The combined light is separated into four beams of light by the coupler 22 being a branching filter. Out of the branched four beams of light, the light from the laser light source LD1 is led through light guides 26 and 27, and the light from the laser light source LD2 is led through light guides 28 and 29. These light guides 26 to 29 are composed of a bundle fiber, i.e. a bundle of a number of optical fibers, or the like. Note that, the light from the laser light sources LD1 and LD2 may directly enter the light guides 26 to 29 without through the combiner 21 and the coupler 22.

The endoscope device 12, being an electronic endoscope, is provided with an endoscope 32, a lighting section 33 for applying the four beams of light led through the light guides 26 to 29 to the observation object, an imaging section 34 for imaging the area to be observed, a handling section 35 for bending the distal end portion of the endoscope 32 and performing another operation for observation, and a connector section 36 for detachably connecting the endoscope 32 to the light source device 11 and the processor device 13.

The endoscope 32 is provided with a soft portion 38, a bending portion 39, and a distal end portion 40 in this order from the side of the handling section 35. The soft portion 38 is flexible so as to be bendable in insertion of the endoscope 32. The bending portion 39 is flexibly bent by a turning operation of an angle knob 35a disposed in the handling section 35. By bending the bending portion 39 in an arbitrary direction and an arbitrary angle according to a body part of the observation object and the like, the distal end portion 40 can be aimed at the desired part to be observed.

The distal end portion 40 has the lighting section 33 and the imaging section 34. The imaging section 34 is provided with one imaging window 42 approximately at the center of the distal end portion 40 to receive light from the observed area. The lighting section 33 has two lighting windows 43 and 44 provided at both sides of the imaging section 34. One of two types of light, i.e. the oxygen saturation level measurement light and the white light is applied to the area to be observed through each of the lighting windows 43 and 44.

Two light projection units 46 and 47 are contained in the recess of the lighting window 43. The light projection unit 46 applies the oxygen saturation level measurement light from the light guide 26 to the area to be observed through a lens 48. In the other light projection unit 47, the excitation light from the light guide 28 is applied to the phosphor 50 to emit the white light. The emitted white light is applied to the area to be observed through a lens 51. Note that, other two light projection units, that is, a light projection unit 53 identical to the above light projection unit 46 and a light projection unit 54 identical to the above light projection unit 47 are contained in the recess of the other lighting window 44.

Figure 3:
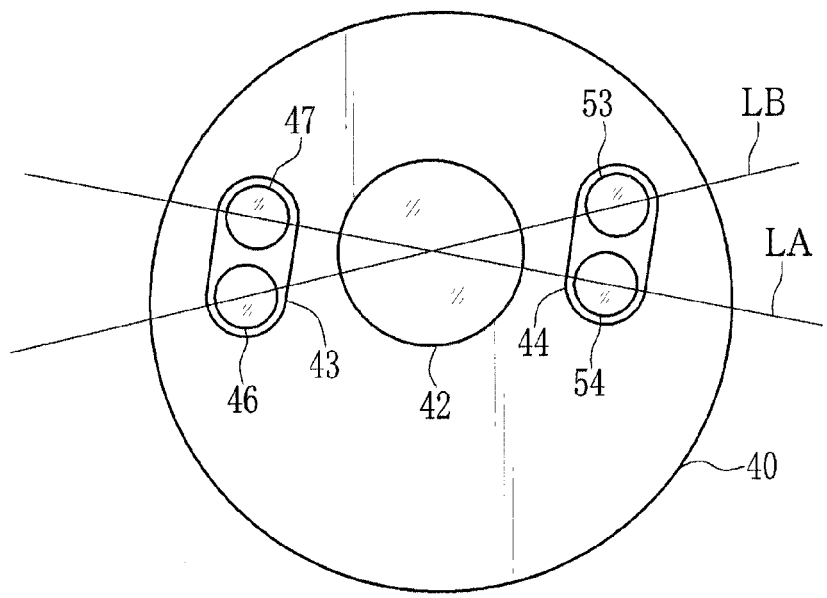
FIG. 3 is a front view showing an end face of a distal end portion.

As shown in FIG. 3, the lighting windows 43 and 44 are disposed at both sides of the imaging window 42 in the distal end portion 40. The four light projection units 46, 47, 53, and 54 are disposed in a staggered manner such that a straight line LA connecting light exit surfaces of the light projection units 47 and 54 having the phosphor 50 and a straight line LB connecting light exit surfaces of the light projection units 46 and 53 without having the phosphor 50 intersect at the center of the imaging window 42. Such a disposition can prevent the occurrence of lighting unevenness.

The phosphor 50 contains a plurality of types of fluorescent substances (for example, a YAG-based fluorescent substance or a fluorescent material such as BAM ($BaMgAl_{10}O_{17}$)) that absorb apart of the excitation light from the laser light source LD2 and emit green to red light. Applying the excitation light to the phosphor 50 produces the white light (pseudo white light) by mixing of the green to red light (fluorescence) emitted from the phosphor 50 and the excitation light passed through the phosphor 50 without being absorbed. The phosphor 50 preferably has an approximately rectangular parallelepiped shape. In this case, the phosphor 50 may be formed by compacting the fluorescent substances by a binder into the rectangular parallelepiped shape, or may be formed of a mixture of the fluorescent substances and a resin such as inorganic glass into the rectangular parallelepiped shape. Note that, the phosphor 50 is known under the trademark of Micro White (MW).

Figure 4:
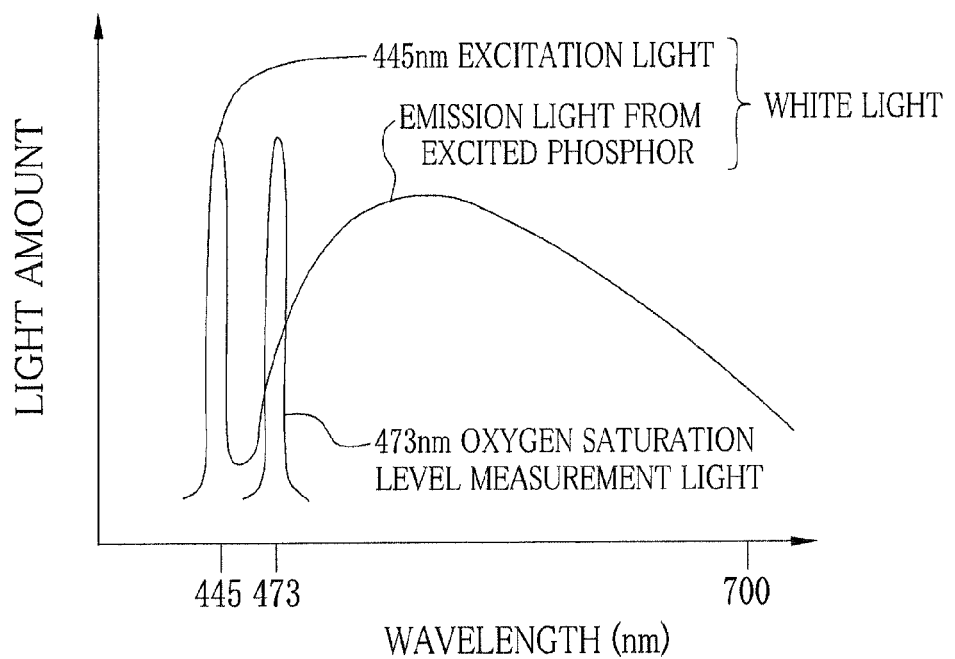
FIG. 4 is a graph showing the light amount distribution of oxygen saturation level measurement light, excitation light, and emission light from an excited phosphor.

Therefore, as shown in FIG. 4, the white light emitted from the light projection units 47 and 54 having the phosphor 50 has an emission spectrum in a wavelength range (for example, 440 to 460 nm) of the excitation light whose center wavelength is 445 nm and a wavelength range of approximately 450 to 700 nm in which the fluorescence emitted by the application of the excitation light has high intensity. On the other hand, the oxygen saturation level measurement light emitted from the light projection units 46 and 53 without having the phosphor 50 has an emission spectrum in a wavelength range (for example, 460 to 480 nm) in the vicinity of a center wavelength of 473 nm.

Note that, in this specification, the white light does not necessarily contain every wavelength component of the visible light, as long as it contains light of specific wavelength bands of R (red), G (green), and B (blue) being primary colors, and the like, such as the pseudo white light described above. In other words, the white light includes, for example, light having a wavelength component from green to red, light having a wavelength component from blue to green, and the like in a broad sense.

An optical system such as an objective lens unit (not shown) is provided in the recess of the imaging window 42 to capture image light of the area to be observed of the observation object. In the recess of the objective lens unit, an imaging device 60, e.g. a CCD (charge coupled device) imaging device or a CMOS (complementary metal-oxide semiconductor) imaging device, is disposed to receive the image light and image the area.

Figure 5:
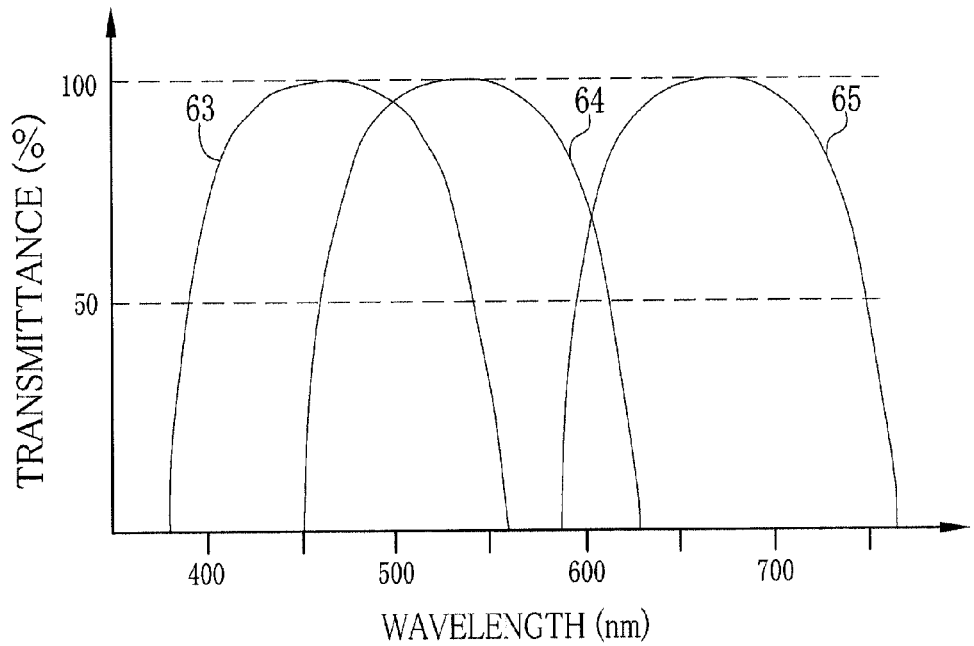
FIG. 5 is a graph of transmittance of color filters of an imaging device.

The imaging device 60 receives the image light from the objective lens unit at its light receiving surface (imaging surface), and performs photoelectric conversion of the received image light to output an imaging signal (analog signal). The imaging device 60 is a color CCD. In the light receiving surface of the imaging device 60, a number of pixel groups each of which includes an R pixel having an R color filter, a G pixel having a G color filter, and a B pixel having a B color filter are arranged into a matrix. The B, G, and R color filters have spectral transmittance represented by curves 63, 64, and 65 of FIG. 5, respectively.

The imaging signal (analog signal) from the imaging device 60 is inputted to an A/D converter 68 through a scope cable 67. The A/D converter 68 converts the imaging signal (analog signal) into an image signal (digital signal) corresponding to its voltage level. The converted image signal is inputted to an image processing unit 73 of the processor device 13 through the connector section 36.

Figure 6A:
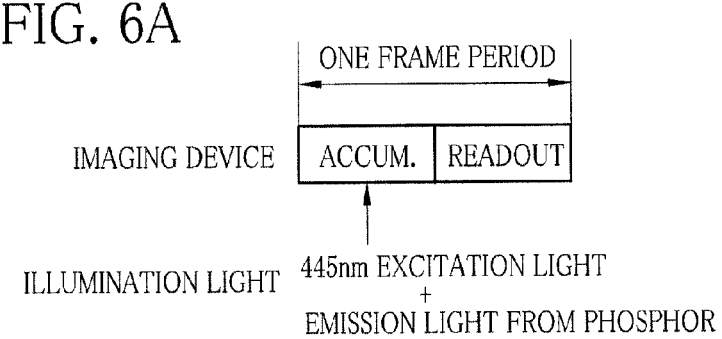
FIG. 6A is an explanatory view of imaging control of the imaging device in a normal observation mode according to a first embodiment.

An imaging controller 70 performs imaging control of the imaging device 60. As shown in FIG. 6A, in the normal observation mode, a step of accumulating electric charge obtained by the photoelectric conversion of the white light (445 nm+fluorescence (represented in this manner because the white light is produced by applying the excitation light of 445 nm to the phosphor 50 in this embodiment)) and a step of reading out the accumulated electric charge, that is, the two steps in total are carried out in one frame period. This is repeated in a predetermined cycle during the normal observation mode. In the normal observation mode, a blue signal Bc outputted from the B pixels of the imaging device 60, a green signal Gc outputted from the G pixels, and a red signal Rc outputted from the R pixels are obtained.

Figure 6B:
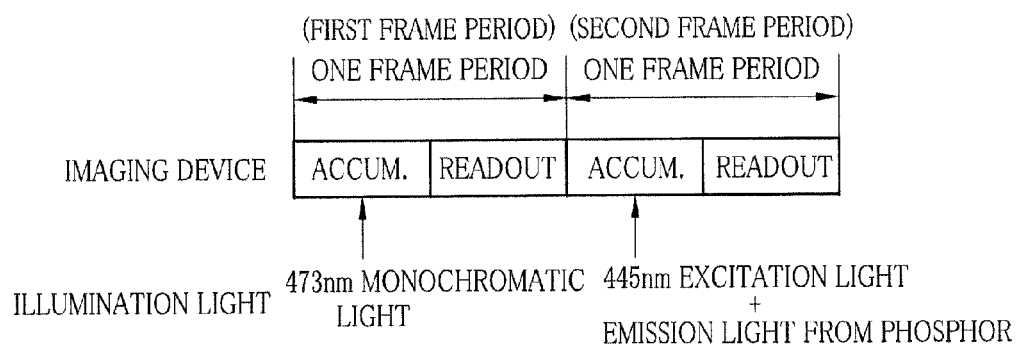
FIG. 6B is an explanatory view of imaging control of the imaging device in a biological information observation mode according to the first embodiment.

On the other hand, in the biological information observation mode, as shown in FIG. 6B, a step of accumulating electric charge obtained by photoelectric conversion of the oxygen saturation level measurement light (narrow band light of 473 nm) and a step of reading out the accumulated electric charge, that is, the two steps in total are carried out in one frame period (first frame period). Next, a step of accumulating electric charge obtained by photoelectric conversion of the white light (445 nm+MW) and a step of reading out the accumulated electric charge, that is, the two steps in total are carried out in one frame period (second frame period). The imaging control of the two frame periods in total is repeated in a predetermined cycle.

In the biological information observation mode, a blue signal B1 outputted from the B pixels of the imaging device 60, a green signal G1 outputted from the G pixels, and a red signal R1 outputted from the R pixels are obtained in the first frame period. A blue signal B2 outputted from the B pixels, a green signal G2 outputted from the G pixels, and a red signal R2 outputted from the R pixels are obtained in the second frame period. Note that, the signals B2, G2, and R2 obtained in the second frame period are the same as the signals Bc, Gc, and Rc obtained in the normal observation mode.

Note that, various channels, which include a forceps channel for inserting a tissue taking device, an air and water feeding channel, and the like, are provided in the handling section 35 and the endoscope 32 of the endoscope device 12, though they are not illustrated.

As shown in FIG. 2, the processor device 13 is provided with a control unit 72, the image processing unit 73, and a storage unit 74. To the control unit 72, the display device 14 and the input device 15 are connected. The control unit 72 controls the operation of the image processing unit 73, the light source controller 20 of the light source device 11, the imaging controller 70 of the endoscope device 12, and the display device 14 based on input information from the switch 17 of the endoscope device 12 and the input device 15.

The image processing unit 73 is provided with a normal light image processor 80, a function information image processor 82, and an emphasized image processor 90. The image processing unit 73 applies a predetermined image process to the image signal from the endoscope device 12.

The normal light image processor 80 produces a normal light image by applying a predetermined image process to the image signal. The normal light image is produced by a video signal composed of a luminance Y and color difference signals Cb and Cr. The green signal Gc obtained in the normal observation mode or the green signal G2 obtained in the biological information observation mode is assigned as the luminance Y. A difference value (Bc−Gc) between the blue signal Bc and the green signal Gc obtained in the normal observation mode, or a difference value (B2−G2) between the blue signal B2 and the green signal G2 obtained in the biological information observation mode is assigned as the color difference signal Cb. A difference value (Rc−Gc) between the red signal Rc and the green signal Gc obtained in the normal observation mode, or a difference value (R2−G2) between the red signal R2 and the green signal G2 obtained in the biological information observation mode is assigned as the color difference signal Cr.

The function information image processor 82 calculates information on a blood volume of the observation object and information on the oxygen saturation level of hemoglobin based on the image signals inputted from the endoscope device 12. The function information image processor 82 also produces a blood volume image representing the blood volume and an oxygen saturation image representing the oxygen saturation level. The function information image processor 82 includes a signal ratio calculator 84, a correlation memory 85, a blood volume and oxygen saturation level calculator 86, a blood volume image generator 87, and an oxygen saturation image generator 88.

The signal ratio calculator 84 calculates a ratio of intensity of each pixel between the image signal of the first frame period and the image signal of the second frame period obtained in the biological information observation mode. The signal ratio of every pixel of the entire screen is calculated. In this embodiment, the signal ratio calculator 84 calculates a signal ratio B1/G2 between the blue signal B1 of the first frame period and the green signal G2 of the second frame period, and a signal ratio R2/G2 between the green signal G2 and the red signal R2 of the second frame period. Note that, the signal ratio may be calculated with respect to the pixels within a blood vessel area, out of the image signal. In this case, the blood vessel area is determined based on the difference between the image signal of the blood vessel area and the image signal of the other area.

Figure 7:
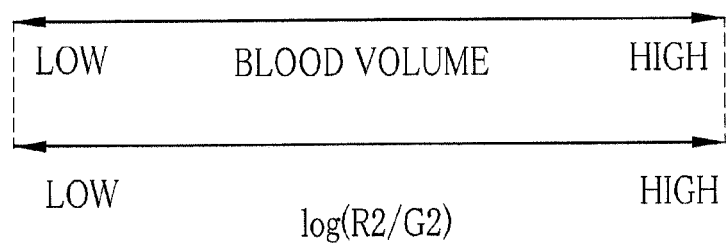
FIG. 7 is an explanatory view showing the correlation between a blood volume and a signal ratio R2/G2.

The correlation memory 85 stores the correlation among the signal ratios B1/G2 and R2/G2, the blood volume, and the oxygen saturation level. As shown in FIG. 7, the correlation between the signal ratio and the blood volume is defined such that the blood volume is increased with increase in the signal ratio R2/G2. This correlation is stored in the form of a one-dimensional table. Note that, the signal ratio is represented in a log scale.

Figure 8:
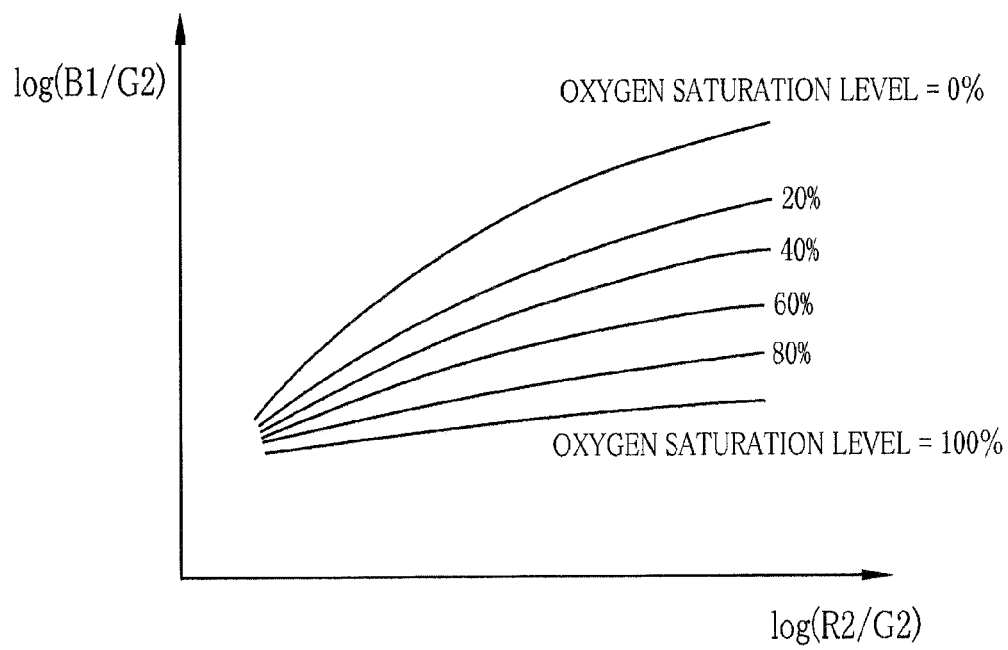
FIG. 8 is a graph showing the correlation among an oxygen saturation level and signal ratios B1/G2 and R2/G2.

On the other hand, the correlation among the signal ratios and the oxygen saturation level is stored in the form of a two-dimensional table in which contour lines of the oxygen saturation level are defined in two-dimensional space as shown in FIG. 8. The position and shape of the contour lines are obtained by physical simulation of light scattering and varied in accordance with the blood volume. For example, variation in the blood volume widens or narrows the distance between the contour lines. Note that, the signal ratios B1/G2 and R2/G2 are depicted in a log scale.

Figure 9:
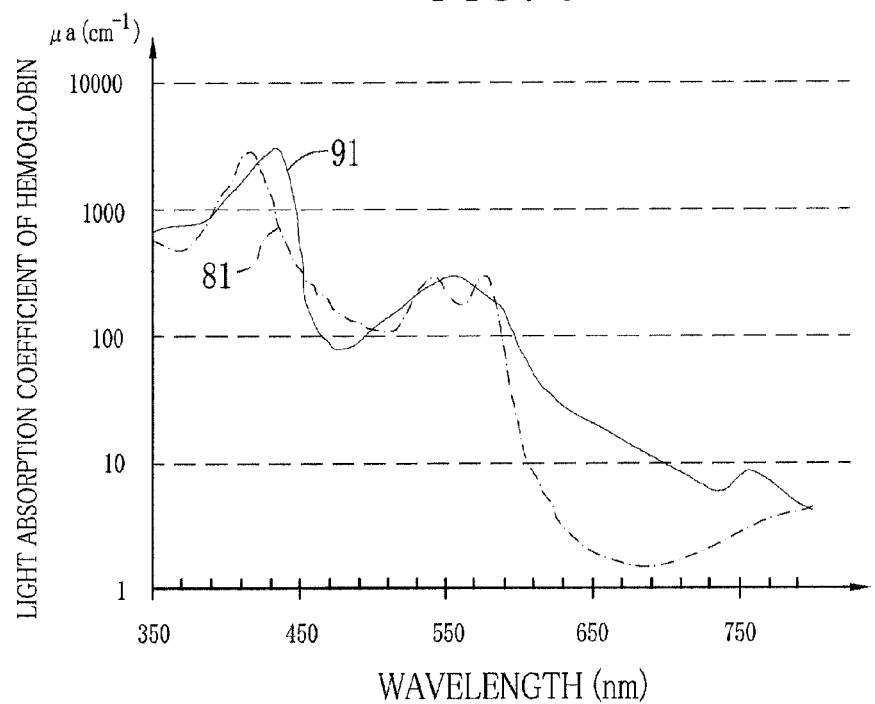
FIG. 9 is a graph of a light absorption coefficient of hemoglobin.

Note that, the above correlation is closely related to a light absorbing property and a light scattering property of oxyhemoglobin and deoxyhemoglobin, as shown in FIG. 9. A line 81 represents a light absorption coefficient of oxyhemoglobin, and a line 91 represents a light absorption coefficient of deoxyhemoglobin. For example, the use of a wavelength of 473 nm at which the light absorption coefficient much differs between oxyhemoglobin and deoxyhemoglobin allows easy obtainment of information on the oxygen saturation level. However, a blue signal that includes a signal corresponding to light of 473 nm highly depends not only on the oxygen saturation level but also on the blood volume. Thus, the use of the signal ratios B1/G2 and R2/G2, which are obtained by the red signal R2 corresponding to light mainly depending on the blood volume and the green signal G2 being a reference signal of the blue signal B1 and the red signal R2, in addition to the blue signal B1, allows obtainment of the oxygen saturation level with high accuracy without depending on the blood volume.

The following three items hold true according to the dependence of the light absorption coefficient of hemoglobin on a wavelength:

(1) In the vicinity of a wavelength of 470 nm (for example, a blue wavelength range having a center wavelength of 470±10 nm), the light absorption coefficient largely varies in accordance with a variation in the oxygen saturation level.

(2) In a green wavelength range of 540 to 580 nm, the light absorption coefficient is averagely insusceptible to the oxygen saturation level.

(3) In a red wavelength range of 590 to 700 nm, the light absorption coefficient seems to vary largely in accordance with the oxygen saturation level, but in actual fact, is insusceptible to the oxygen saturation level because a value of the light absorption coefficient itself is very small.

Figure 10:
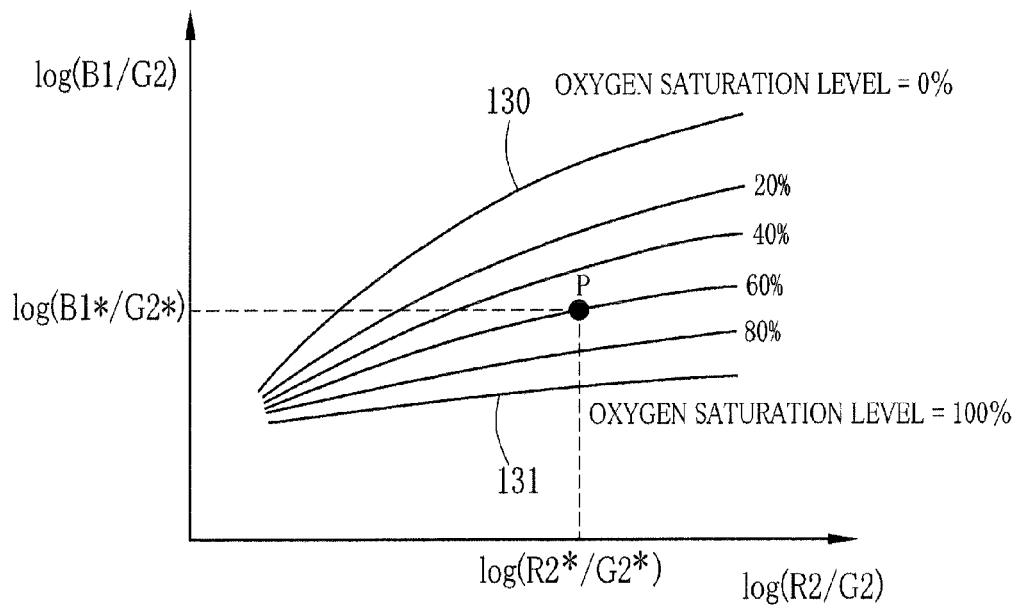
FIG. 10 is an explanatory view showing a method of calculating the oxygen saturation level from the signal ratios in the graph of FIG. 8.

The blood volume and oxygen saturation level calculator 86 calculates both the blood volume and the oxygen saturation level of each pixel by using the correlation stored in the correlation memory 85 and the signal ratios B1/G2 and R2/G2 obtained in the signal ratio calculator 84. The blood volume is a value that corresponds to the signal ratio R2/G2 obtained in the signal ratio calculator 84 in the one-dimensional table of the correlation memory 85. As for the oxygen saturation level, on the other hand, as shown in FIG. 10, a point P that corresponds to signal ratios B1*/G2* and R2*/G2* obtained in the signal ratio calculator 84 is determined in the two-dimensional space.

If the corresponding point P is situated between a lower limit line 130 representing an oxygen saturation level of 0% and an upper limit line 131 representing an oxygen saturation level of 100%, the oxygen saturation level is determined according to a percentile of the contour line on which the corresponding point P is situated. Taking FIG. 10 as an example, the point P is situated on the contour line of 60%, so the oxygen saturation level is 60%. Note that, if the corresponding point is situated above the lower limit line 130, the oxygen saturation level is determined to be 0%. If the corresponding point is situated below the upper limit line 131, the oxygen saturation level is determined to be 100%. Note that, in such cases, the oxygen saturation level may be judged to have low reliability and not be displayed.

The blood volume image generator 87 produces a blood volume image, which represents the blood volume obtained by the blood volume and oxygen saturation level calculator 86 with artificial colors. The blood volume image is composed of the video signal containing the luminance Y and the color difference signals Cb and Cr. The green signal G2, which includes information on reflected light in a wavelength band in which hemoglobin absorbs light at a relatively high rate, is assigned as the luminance Y. Since the luminance Y defines the total brightness of the artificial color image, assigning the green signal G2 as the luminance Y improves visibility of projections and depressions of mucosa, a blood vessel, and the like.

On the other hand, signal values corresponding to the blood volume in accordance with a color table 87a are assigned as the color difference signals Cb and Cr. The color table 87a is defined such that a value of the color difference signal Cb decreases with increase in the blood volume, and a value of the color difference signal Cr increases with increase in the blood volume. Therefore, the blood volume image becomes reddish at a part of the large blood volume. With decrease in the blood volume, red chroma decreases and approaches monochrome.

The oxygen saturation image generator 88 produces the oxygen saturation image, which represents the oxygen saturation level obtained by the blood volume and oxygen saturation level calculator 86 with artificial colors. The oxygen saturation image is composed of a video signal containing the luminance Y and the color difference signals Cb and Cr, just as with the blood volume image. The green signal G2, which defines the total brightness and facilitates improving visibility of projections and depressions of mucosa, a blood vessel, and the like, is assigned as the luminance Y. Signal values corresponding to the oxygen saturation level in accordance with a color table 88*a* are assigned as the color difference signals Cb and Cr.

According to the color table 88*a*, the color difference signal Cr is defined to be a positive signal value and the color difference signal Cb is defined to be a negative signal value at a high oxygen saturation level, and on the contrary, the color difference signal Cr is defined to be a negative signal value and the color difference signal Cb is defined to be a positive signal value at a low oxygen saturation level. The magnitude relation between the signal value of the color difference signal Cr and the signal value of the color difference signal Cb is reversed at a middle oxygen saturation level. According to this definition, the color of the oxygen saturation image is changed from bluish, sky bluish, greenish, yellowish, orangish, to reddish as the oxygen saturation level increases.

Figure 11:
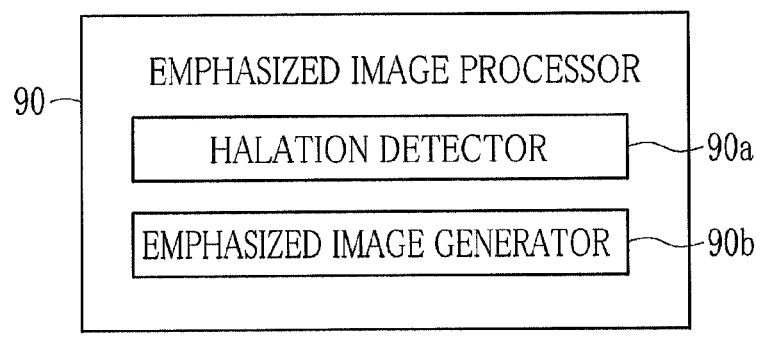
FIG. 11 is a block diagram showing the internal structure of an emphasized image processor according to the first embodiment.

As shown in FIG. 11, the emphasized image processor 90 includes a halation detector 90*a* and an emphasized image generator 90*b*. The halation detector 90*a* detects whether or not a halation area in which a calculation result of the blood volume and oxygen saturation level calculator 86 becomes abnormal exists in the blood volume image or the oxygen saturation image. The emphasized image generator 90*b* superimposes the normal light image on the blood volume image or the oxygen saturation image having no halation area to produce an emphasized image. In the emphasized image, a first abnormal area in which a calculation result of the blood volume and oxygen saturation level calculator 86 is likely to be abnormal is emphasized.

Figure 12:
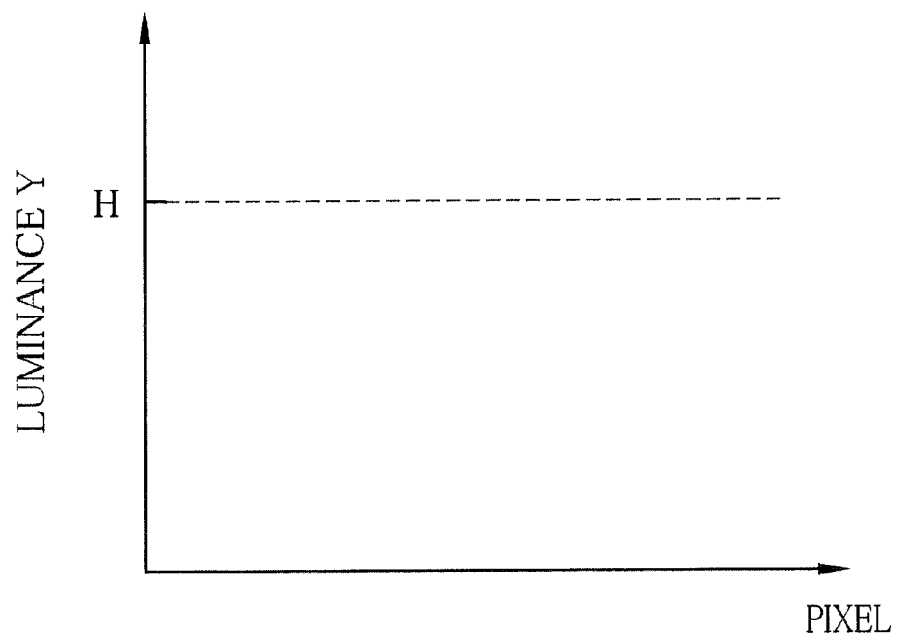
FIG. 12 is a graph showing a halation value.
Figure 13:
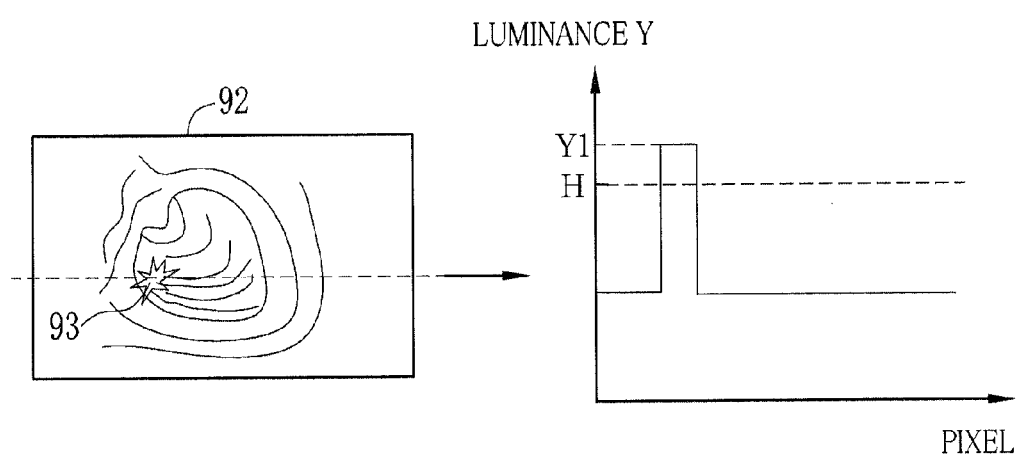
FIG. 13 is an explanatory view showing an oxygen saturation image having a halation area and a luminance of the halation area in a normal light image.

The halation detector 90*a* detects whether or not the halation area that has a luminance Y of a halation value H or more, as shown in FIG. 12, exists in the blood volume image or the oxygen saturation image. Taking an oxygen saturation image 92 shown in FIG. 13 as an example, an area 93 has a luminance Y1 over the halation value H, and hence is detected as a halation area 93. The oxygen saturation image 92 having the halation area 93 is displayed on the display device 14 as is. The halation area 93 is seen brightly in the display device 14 because of the extremely high luminance Y1. Therefore, an operator seeing the display device 14 can grasp at sight that the calculation result of the oxygen saturation level is abnormal i.e. unreliable in the halation area.

The emphasized image generator 90*b* produces an emphasized blood volume image by superimposing the normal light image on the blood volume image in which no halation area has detected, and produces an emphasized oxygen saturation image by superimposing the normal light image on the oxygen saturation image in which no halation area has detected. The emphasized blood volume image or the emphasized oxygen saturation image after being produced is displayed on the display device 14. In superimposing the images, the luminance Y of the normal light image is added to the luminance Y of the blood volume image or the oxygen saturation image, while the color difference signals Cb and Cr of the normal light image are not added to the color difference signals Cb and Cr of the blood volume image or the oxygen saturation image. Thus, only brightness is varied in the blood volume image or the oxygen saturation image without changing its color. Note that, also in a case where there is a halation area detected, the emphasized blood volume image or the emphasized oxygen saturation image may be produced as with above.

Figure 14:
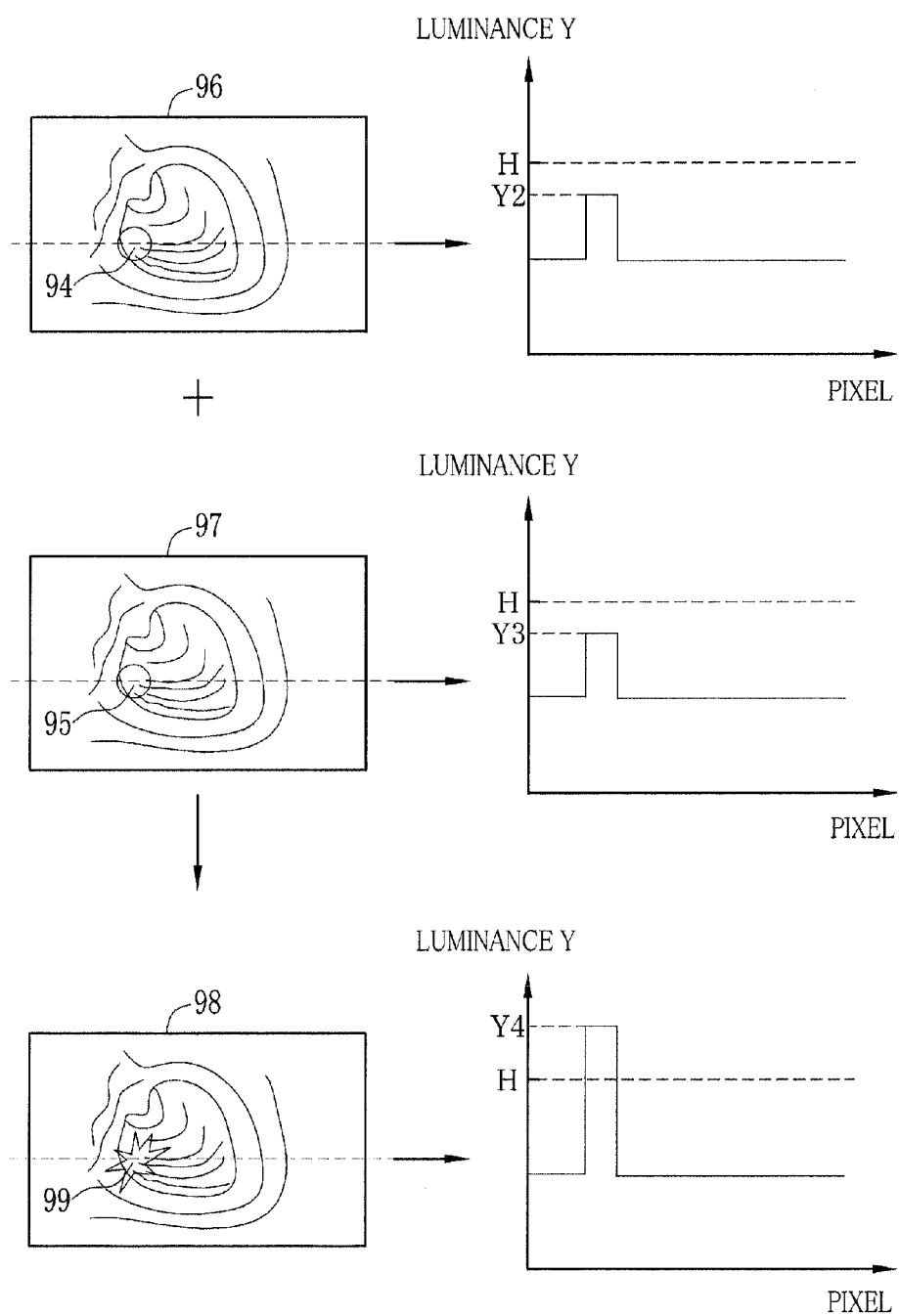
FIG. 14 is an explanatory view showing a method of producing an emphasized oxygen saturation image according to the first embodiment.

For example, as shown in FIG. 14, in the case of superimposing a normal light image 97 having an area 95 having a luminance Y3 slightly less than the halation value H on an oxygen saturation image 96 having an area 94 having a luminance Y2 slightly less than the halation value H (the areas 94 and 95 are in approximately the same position), the luminance Y3 of the normal light image 97 is added to the luminance Y2 of the oxygen saturation image 95 to produce an emphasized oxygen saturation image 98. In the emphasized oxygen saturation image 98 after being overlaid, an area 99 corresponding to the areas 94 and 95 is emphasized because its luminance Y4 exceeds the halation value H.

The area 99 is seen as brightly as the halation area, or a little less brightly than the halation area. Thus, the area 99 is determined to be the first abnormal area 99 in which it is grasped at sight that the calculation result of the oxygen saturation level is abnormal or is likely to be abnormal, i.e. unreliable. Note that, the luminance Y4 of the first abnormal area 99 is larger than the halation value H in FIG. 14, but the luminance Y after the superimposition does not necessarily exceed the halation value H. For example, the luminance Y may get close to the halation value H by the superimposition.

Figure 15:
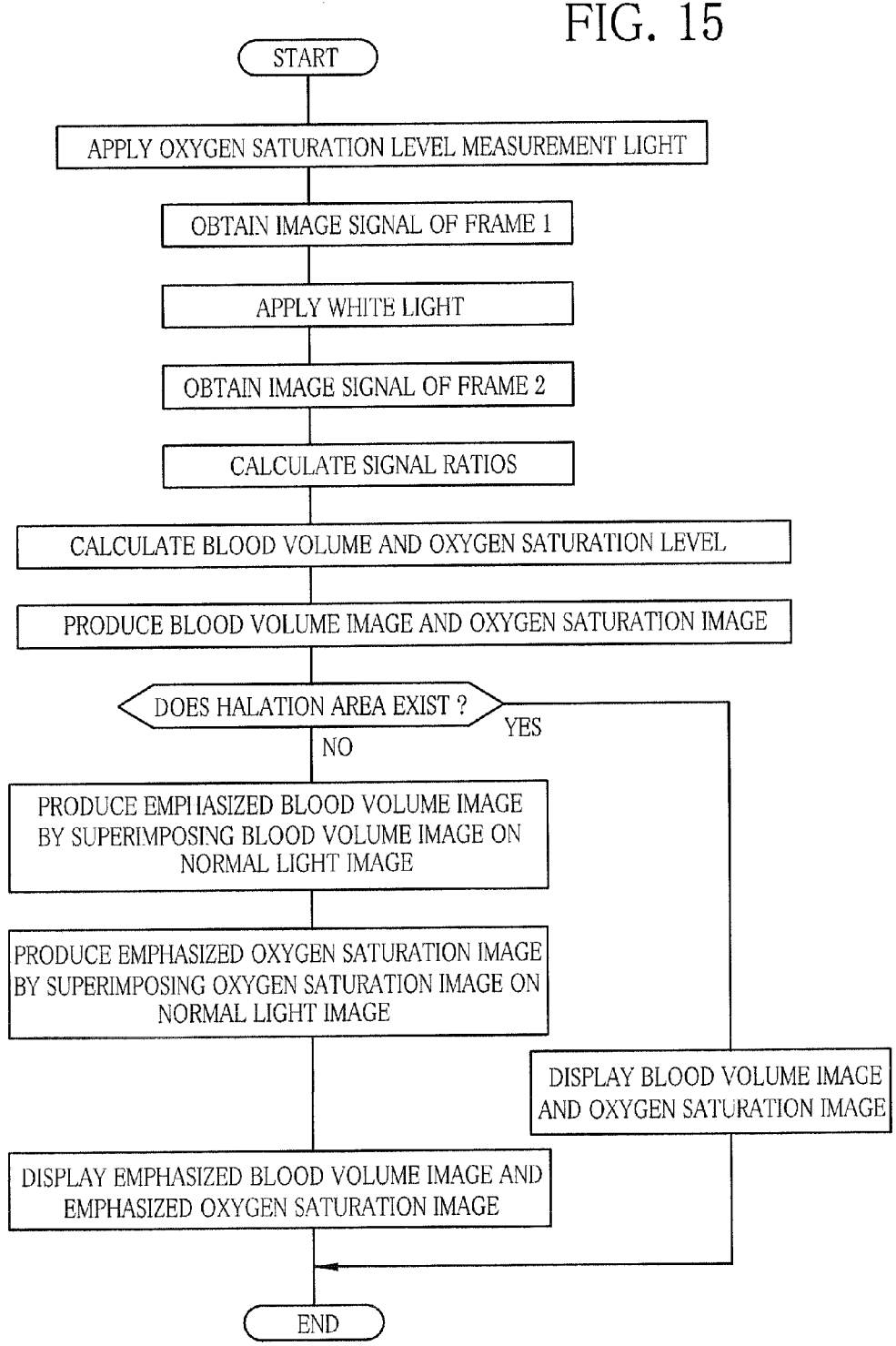
FIG. 15 is a flowchart showing an operation flow in the biological information observation mode.

Next, the operation of the present invention will be described with referring to a flowchart of FIG. 15. In the normal observation mode, the endoscope 32 is inserted into a human body, for example, a digestive canal. The distal end portion is aimed at the desired area to be observed by the operation of the angle knob 35*a*, to perform normal observation. In the normal observation, the color normal light image of the observed area captured under irradiation with the white light is displayed on the display device 14.

When the observed area seems to be a lesion, the endoscope system 10 is put into the biological information observation mode by the operation of the switch 17 of the endoscope device 12. Thus, the oxygen saturation level measurement light, being the narrow band light having a center wavelength of 473 nm, is applied from the distal end portion 40 to the observation object. The imaging device 60 having the B pixels, the G pixels, and the R pixels performs the photoelectric conversion of the light reflected from the observation object. Thus, the image signal of the first frame including the blue signal B1, the green signal G1, and the red signal R1 is obtained (frame 1).

After the image signal of the first frame is obtained, the excitation light having a center wavelength of 445 nm is applied to the phosphor 50 of the distal end portion 40. Accordingly, the white light is emitted from the phosphor 50, and the emitted white light is applied to the observation object. The imaging device 60 captures the light reflected from the observation object, so the image signal of the second frame including the blue signal B2, the green signal G2, and the red signal R2 is obtained (frame 2).

Upon obtaining the image signal of the second frame, the normal light image is produced from the image signals B2, G2, and R2 of the second frame. Also, the blood volume and the oxygen saturation level are calculated from the image signal B1 of the first frame and the image signals G2 and R2 of the second frame. First, the signal ratios B1/G2 and R2/G2 are calculated with respect to a pixel in the same position between the image signal of the first frame and the image signal of the second frame. After the calculation of the signal ratios, the blood volume and the oxygen saturation level corresponding to the signal ratios B1/G2 and R2/G2 are obtained from the correlation stored in the correlation memory 85. The blood volume and the oxygen saturation level are obtained with respect to every pixel in the screen.

Upon calculating the blood volume and the oxygen saturation level of every pixel, the color difference signals Cb and Cr corresponding to the blood volume are obtained with referring to the color table 87a of the blood volume image generator 87. Based on the obtained color difference signals Cb and Cr and the luminance Y as which the green signal G2 is assigned, the blood volume image is produced in which the blood volume is represented with the artificial colors. As with the blood volume image, the oxygen saturation image in which the oxygen saturation level is represented with the artificial colors is produced using the color table 88a.

Next, it is detected whether or not the halation area that has the luminance Y over the halation value H exists in the produced blood volume image and the oxygen saturation image. The blood volume image and the oxygen saturation image having the halation area are displayed on the display device 14 side by side. If no halation area has been detected, on the other hand, the emphasized blood volume image having the increased luminance Y is produced by superimposing the normal light image on the blood volume image, and the emphasized oxygen saturation image having the increased luminance Y is produced by superimposing the normal light image on the oxygen saturation image. Since these emphasized blood volume image and the emphasized oxygen saturation image have the increased luminance Y, the first abnormal area is produced in which the luminance Y exceeds or gets close to the halation value H.

As described above, the blood volume image and the oxygen saturation image having the halation area are displayed on the display device 14 as is without increasing its luminance Y. Thus, it is possible to notify the operator that the calculation result of the halation area is abnormal, while the calculation result of the other area is normal. On the other hand, as for the blood volume image and the oxygen saturation image having no halation area, the normal light image is overlaid thereon to produce the emphasized blood volume image and the emphasized oxygen saturation image. The produced emphasized blood volume image and the produced emphasized oxygen saturation image are displayed on the display device 14. Therefore, it is possible to notify the operator that the calculation result of the first abnormal area in the emphasized blood volume image and the emphasized oxygen saturation image is abnormal or likely to be abnormal, while the calculation result of the other area is normal. An operation sequence described above is repeated as long as the endoscope system 10 is put in the biological information observation mode.

Figure 16:
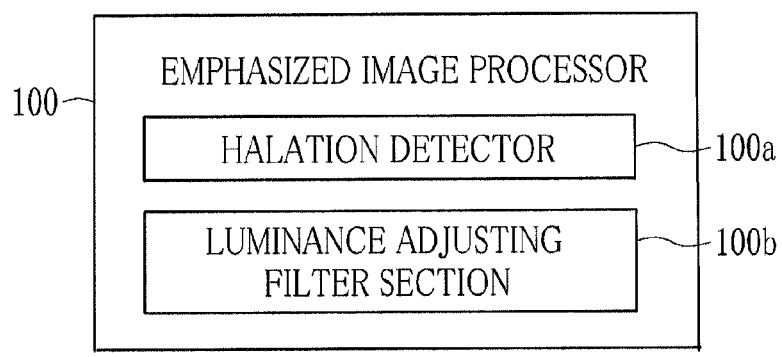
FIG. 16 is a block diagram showing the internal structure of an emphasized image processor according to a second embodiment.

In a second embodiment of the present invention, a first abnormal area in which the calculation result of the blood volume and oxygen saturation level calculator 86 is likely to be abnormal because of too large luminance Y is brightened to emphasize the first abnormal area itself by its brightness, while a second abnormal area in which the calculation result of the blood volume and oxygen saturation level calculator 86 is likely to be abnormal because of too small luminance Y is darkened to emphasize the second abnormal area by its darkness. An emphasized image processor 100 as shown in FIG. 16, instead of the emphasized image processor 90, performs an emphasizing process of the second embodiment. Note that, components other than the emphasized image processor 100 are identical to those of the first embodiment and therefore the description thereof will be omitted.

The emphasized image processor 100 includes a halation detector 100a, which is identical to the halation detector 90a of the first embodiment, and a luminance adjusting filter section 100b. The luminance adjusting filter section 100b applies luminance adjusting filtering to the blood volume image and the oxygen saturation image in which the halation detector 100a has not detected the halation area. By the luminance adjusting filtering, the first abnormal area is further brightened and the second abnormal area is further darkened.

Figure 17:
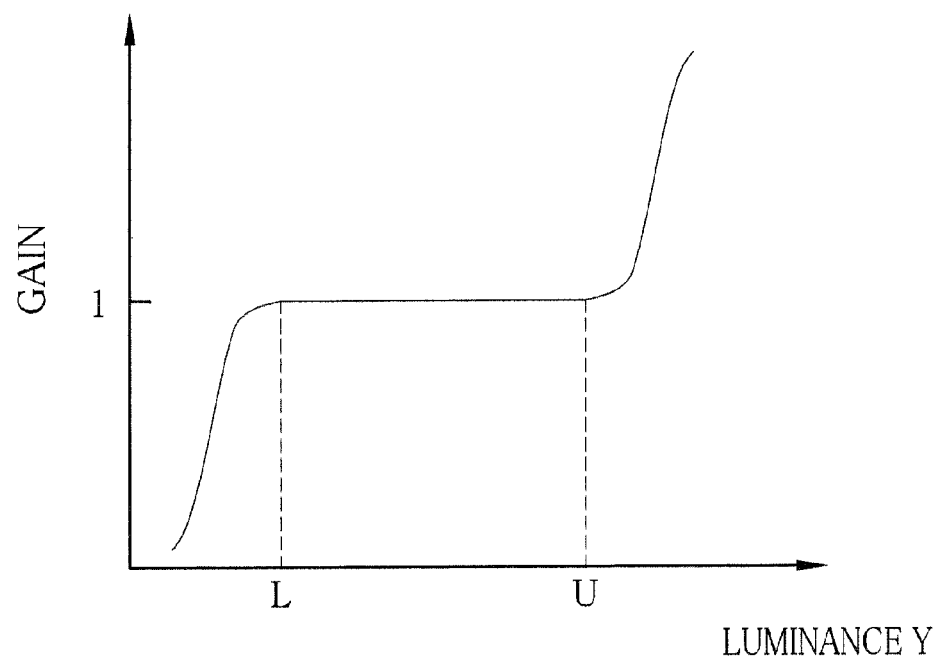
FIG. 17 is a graph showing the relation between a gain and a luminance Y.

The luminance adjusting filter section 100b has a gain table as shown in FIG. 17. According to the luminance adjusting filtering using this gain table, when the luminance Y is more than a certain upper limit value U, the luminance Y increases with a gain of "1" or more. When the luminance Y is less than a certain lower limit value L, the luminance Y decreases with a gain of "1" or less. In the other cases, the luminance Y is maintained as is with a gain of "1". An emphasized blood volume image that is obtained by applying the luminance adjusting filtering to the blood volume image and an emphasized oxygen saturation image that is obtained by applying the luminance adjusting filtering to the oxygen saturation image are displayed on the display device 14.

Figure 18:
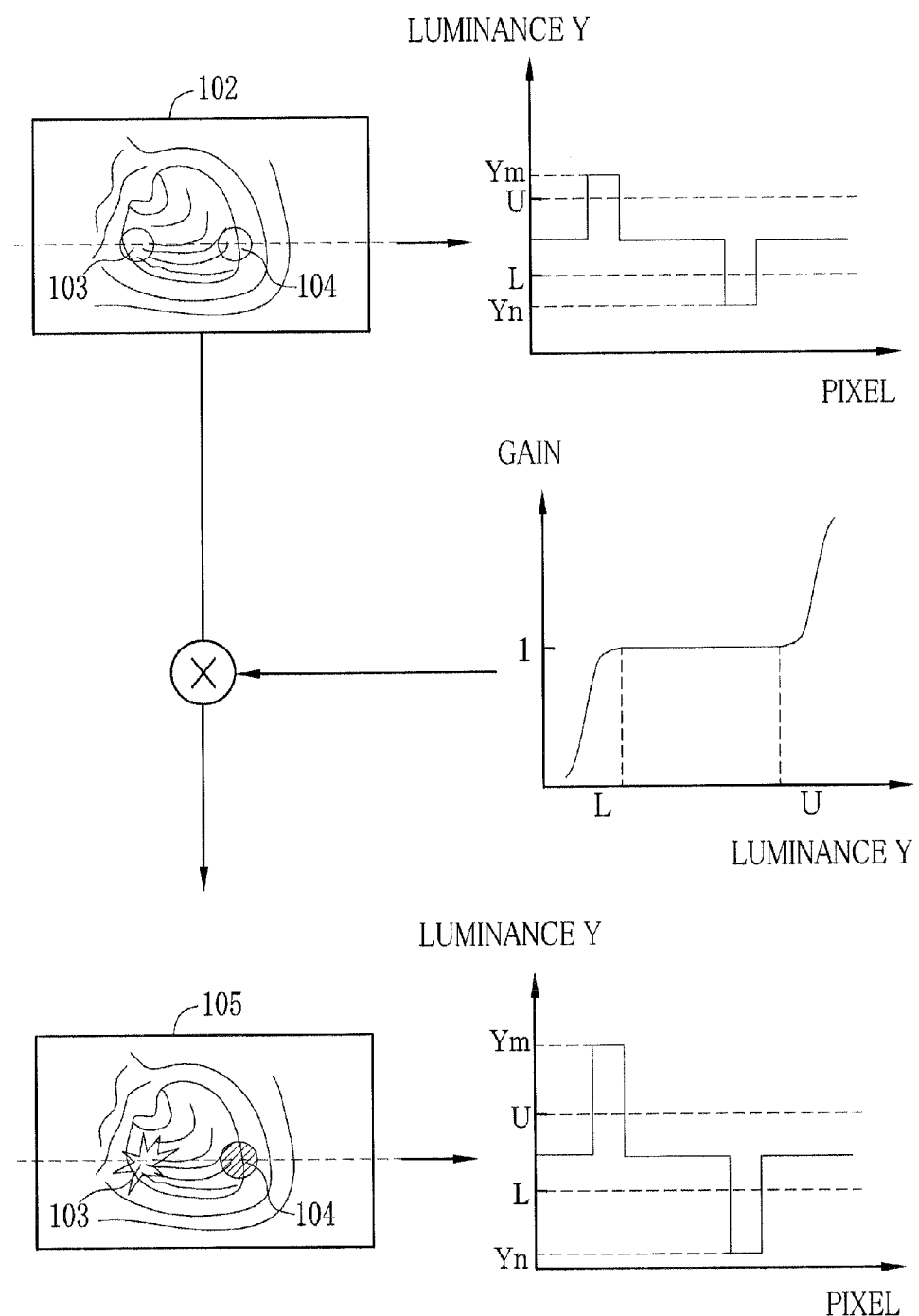
FIG. 18 is an explanatory view showing a method of producing an emphasized oxygen saturation image according to the second embodiment.

For example, as shown in FIG. 18, when an oxygen saturation image 102 has a bright first abnormal area 103 having a luminance Ym more than the upper limit value U and a dark second abnormal area 104 having a luminance Yn less than the lower limit value L, the luminance adjusting filtering is applied to the oxygen saturation image 102 to obtain an emphasized oxygen saturation image 105. In the emphasized oxygen saturation image 105, the luminance Ym of the first abnormal area 103 is further increased, while the luminance Yn of the second abnormal area 104 is further decreased. In the emphasized oxygen saturation image 105 displayed on the display device 14, the first abnormal area 103 is extremely bright, while the second abnormal area 104 is extremely dark. Emphasizing the first abnormal area 103 by its brightness and the second abnormal area 104 by its darkness makes it possible for the operator to grasp at sight that the oxygen saturation level of the first and second abnormal areas 103 and 104 is unreliable.

Note that in the above first embodiment, even in a case where the halation area is detected in the blood volume image and the oxygen saturation image, the first abnormal area may be emphasized by superimposing the normal light image on the blood volume image and the oxygen saturation image. Also, in the above second embodiment, even in a case where the halation area is detected in the blood volume image and the oxygen saturation image, the first and second abnormal area may be emphasized by luminance adjusting filtering.

In the above second embodiment, the first and second abnormal areas are emphasized by adjusting the luminance Y. However, a pixel value itself may be adjusted instead of the luminance Y. The first and second abnormal areas are emphasized by both the brightness and the darkness, but may be emphasized by only one of the brightness and the darkness.

Figure 19:
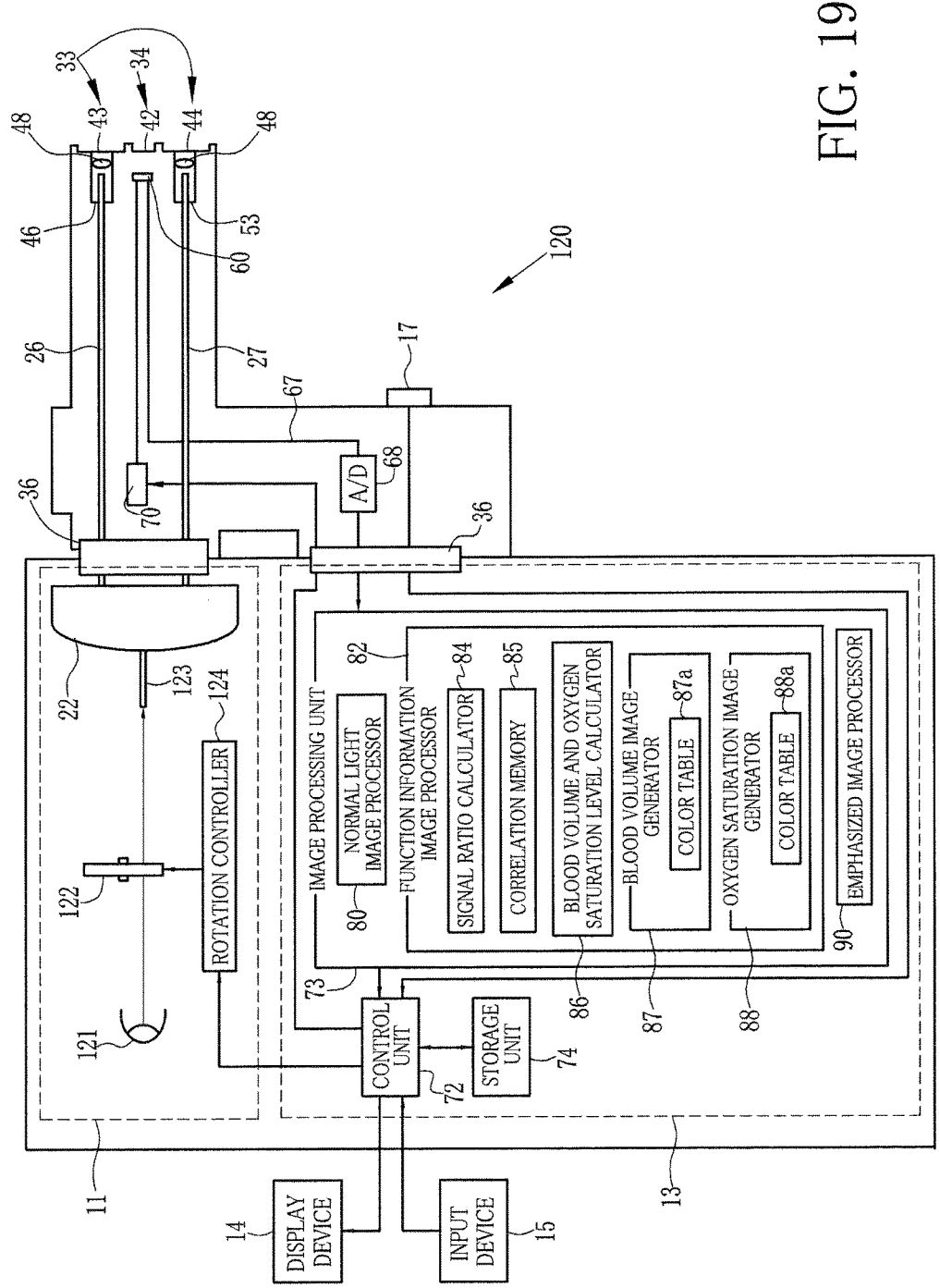
FIG. 19 is a schematic view showing the internal structure of an endoscope system of a rotary filter type.
Figure 20:
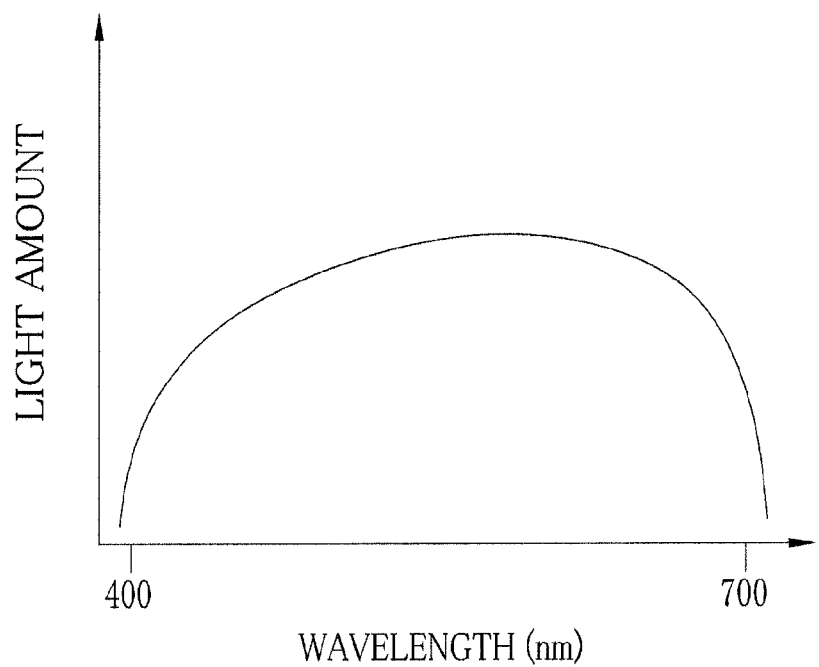
FIG. 20 is a graph of the light amount distribution of white light.

In a third embodiment of the present invention, the illumination light needed for producing the blood volume image and the oxygen saturation image is produced using a white light source such as a xenon lamp and a rotating filter having a wavelength separation function. As shown in FIG. 19, an endoscope system 120 according to the third embodiment is provided with a broad band light source 121, a rotating filter 122, an optical fiber 123, and a rotation controller 124, instead of the laser light sources LD1 and LD2, the light source controller 20, and the combiner 21 of the first and second embodiments. The broad band light source 121, such as a xenon light source, emits white light having spectral intensity as shown in FIG. 20. The rotating filter 122 transmits a wavelength component of the oxygen saturation level measurement light out of the white light, or transmits the entire white light. The light transmitted through the rotating filter 122 enters the optical fiber 123. The rotation controller 124 controls rotation of the rotating filter 122.

The light that has entered the optical fiber 123 is split in two beams of light by the coupler 22. The split two beams of light are applied from the light projection units 46 and 53 to the observation object through the light guides 26 and 27, respectively. Note that, the other components of the endoscope system 120 are identical to those of the endoscope system 10, so the description thereof will be omitted.

Figure 21:
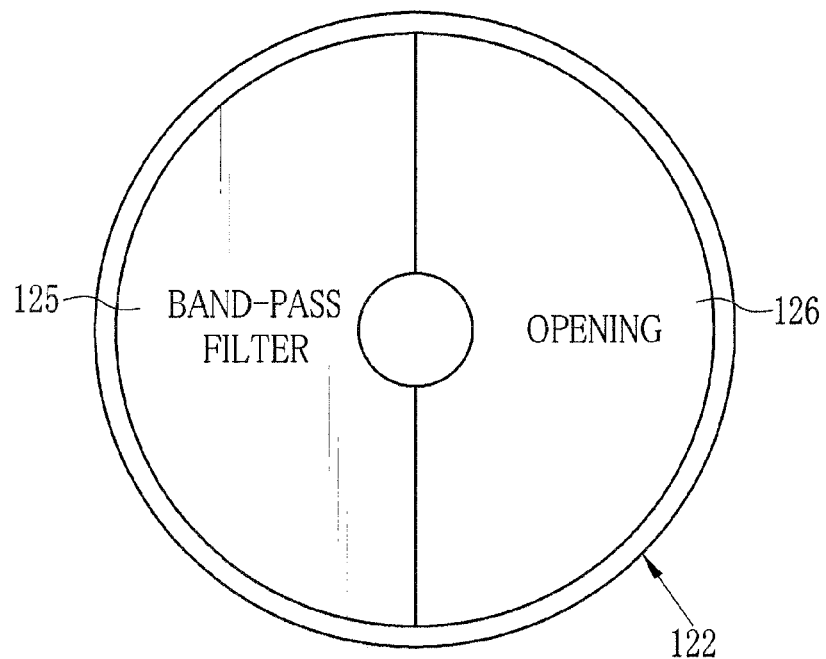
FIG. 21 is a plan view of a rotary filter.

As shown in FIG. 21, the rotating filter 122 has a band-pass filter 125 for transmitting the oxygen saturation level measurement light (see FIG. 4) having a center wavelength of 473 nm out of the white light, and an opening 126 for transmitting the white light as is. Thus, by the rotation of the rotating filter 122, the oxygen saturation level measurement light and the white light are alternately applied to the observation object. At this time, as with the first and second embodiments, the image signal of the first frame is obtained under irradiation with the oxygen saturation level measurement light, and the image signal of the second frame is obtained under irradiation with the white light. The normal light image is produced from the image signal of the second frame, and the blood volume image and the oxygen saturation image are produced from the image signals of the first and second frames, just as with the first and second embodiments. Note that, the band-pass filter 125 preferably transmits light in a wavelength range of 460 to 480 nm.

Just as with the first and second embodiments, the emphasized blood volume image in which an area whose calculation result of the blood volume is abnormal or likely to be abnormal is emphasized is produced by superimposing the normal light image on the blood volume image. In addition, the emphasized oxygen saturation image in which an area whose calculation result of the oxygen saturation level is abnormal or likely to be abnormal is emphasized is produced by superimposing the normal light image on the oxygen saturation image.

Note that, since the white light has a spectral intensity property as shown in FIG. 20, the blue signal B2 contains a signal corresponding to light in a wavelength range of 400 to 530 nm. The green signal G2 contains a signal corresponding to light in a wavelength range of 540 to 580 nm. The red signal R2 contains a signal corresponding to light in a wavelength range of 590 to 700 nm.

Note that, out of the light of three wavelengths used in calculating the blood volume and the oxygen saturation level, part of the light may be light of a semiconductor light source just as with the first and second embodiments, while the other light may be light split from broad band light BB of the white light source such as the xenon lamp by wavelength separation.

Figure 22:
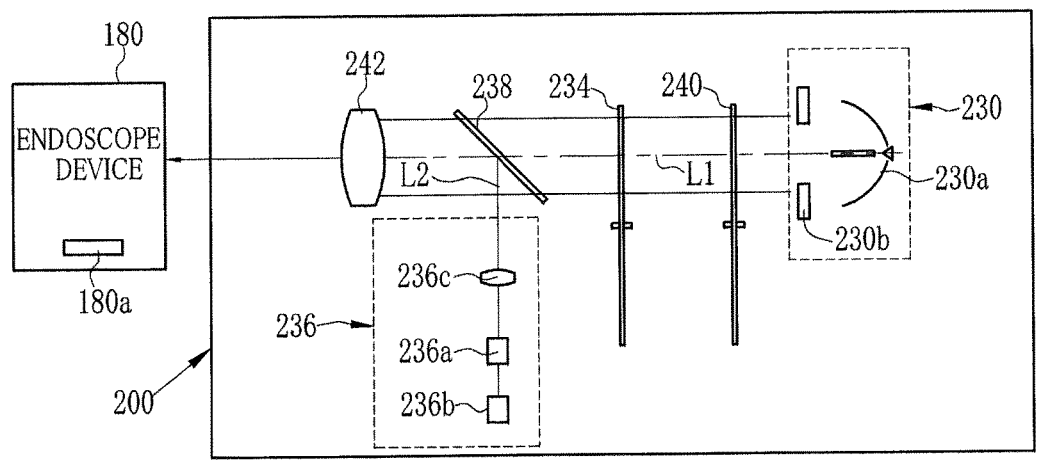
FIG. 22 is a schematic view of a light source device that produces light using a semiconductor light source and produces light by wavelength separation of broad band light from a white light source such as a xenon lamp.

In a fourth embodiment of the present invention, a light source device 200 as shown in FIG. 22 is adopted. Light produced in the light source device 200 is applied to an endoscope device 180. This endoscope device 180 has almost the same structure as the endoscope device 12 of the first and second embodiments, except that there is no phosphor 50 in the lighting section 33 at the distal end portion. Therefore, the light from the light source device 200 is applied to the observation object as is through the endoscope device 180.

The structure of an imaging device 180*a* and the operation of the imaging controller 70 in the endoscope device 180 differ from those of the first and second embodiments. In the processor device 13, a method for producing the normal light image in the normal light image processor 80 is different from that of the first and second embodiments, and signals used in the function information image processor 82 are different from those used in the first and second embodiments. Only matters different from the above first and second embodiments will be hereinafter described, and the description of the others will be omitted.

The light source device 200 is provided with a white light source unit 230 for emitting broad band light BB (400 to 700 nm), a rotary filter 234 for color separating the broad band light BB from the white light source unit 230 into three colors of light of B, G, and R and sequentially applies the light of each color to the endoscope device 180, a semiconductor light source unit 236 for emitting blue narrow band light BN, a light combining section 238 for merging an optical path L2 of the blue narrow band light BN into an optical path L1 of the broad band light BB, and a shutter plate 240 for blocking the optical path of the broad band light BB between the white light source 230 and the rotary filter 234 in predetermined timing.

The white light source unit 230 includes a white light source 230*a* for radiating the broad band light BB and an aperture stop 230*b* for adjusting a light amount of the broad band light BB. The white light source 230*a* is composed of a xenon lamp, a halogen lamp, a metal halide lamp, or the like. The degree of opening of the aperture stop 230*b* is adjusted by a light amount controller (not shown).

Figure 23:
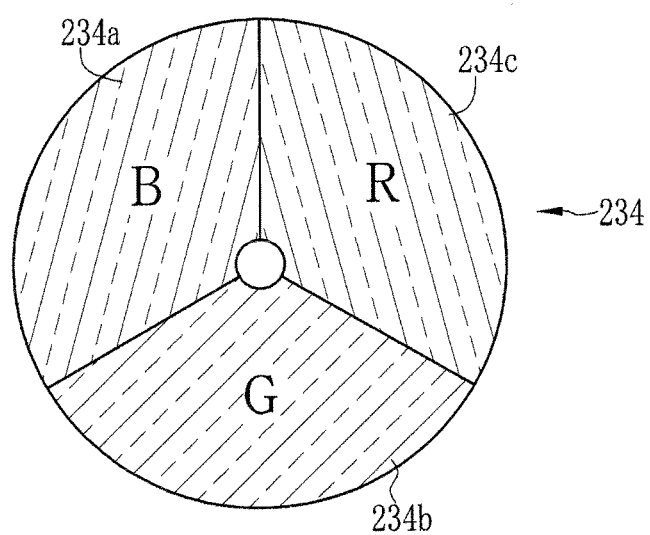
FIG. 23 is a plan view of a rotary filter having a B filter, a G filter, and an R filter arranged in a circumferential direction.

As shown in FIG. 23, the rotary filter 234 is rotatable so that a B filter 234*a*, a G filter 234*b*, and an R filter 234*c* are selectively inserted in the optical path L1 of the broad band light BB. The rotary filter 234 is in a disk shape and partitioned in a circumferential direction into three sectors each having a central angle of 120°. The B filter 234*a*, the G filter 234*b*, and the R filter 234*c* are provided in each of the sectors.

Figure 24:
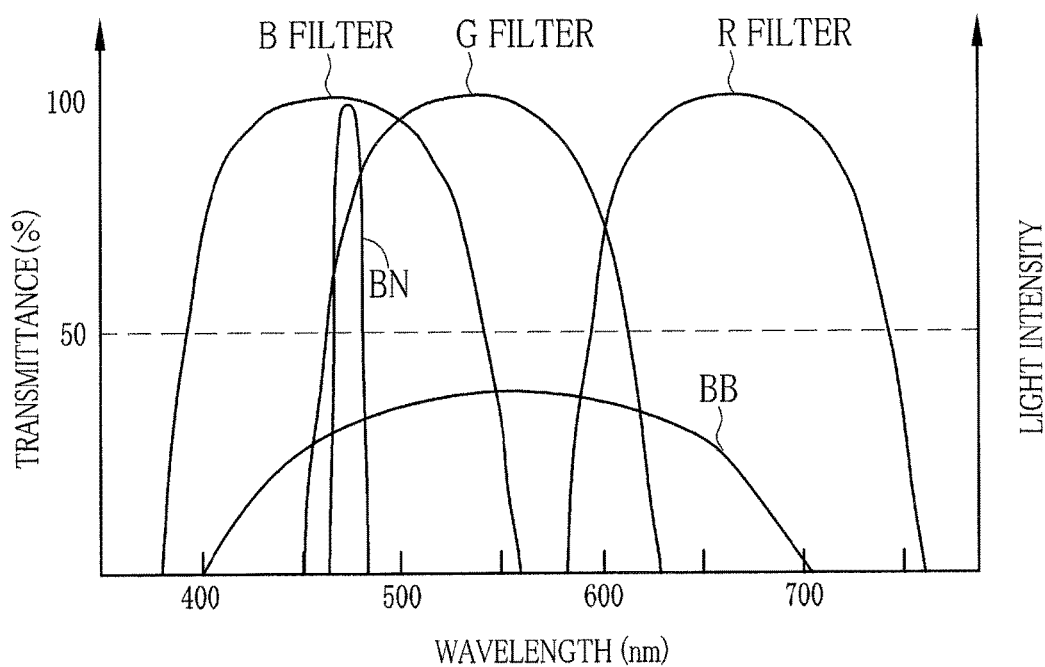
FIG. 24 is a graph showing spectral transmittance of the B filter, the G filter, and the R filter, and the light intensity of blue narrow band light.

As shown in FIG. 24, the B filter 234*a* transmits B light in a blue wavelength band out of the broad band light BB. The G filter 234*b* transmits G light in a green wavelength band out of the broad band light BB. The R filter 234*c* transmits R light in a red wavelength band out of the broad band light BB. Therefore, by the rotation of the rotary filter 234, the B light, the G light, and the R light are sequentially projected from the rotary filter 234.

The semiconductor light source unit 236 has a laser light source 236*a* and a light source controller 236*b*. As shown in FIG. 24, the laser light source 236*a* emits blue narrow band light BN having a center wavelength of 473 nm. The laser light source 236*a* turns on and off under the control of the light source controller 236*b*. The light source controller 236*b* is controlled by the control unit 72 of the processor device 13. The blue narrow band light BN emitted from the laser light source 236*a* is projected to the light combining section 238 through a condenser lens 236*c*.

The light combining section 238, being a dichroic mirror, transmits light from the rotary filter 234 as is, while reflecting the blue narrow band light BN from the semiconductor light source unit 236, so that the optical path L2 of the blue narrow band light BN is merged into the optical path L1 of the broad band light BB. The merged light exits from the light combining section 238 and is supplied to the endoscope device 180 through a condenser lens 242.

Figure 25:
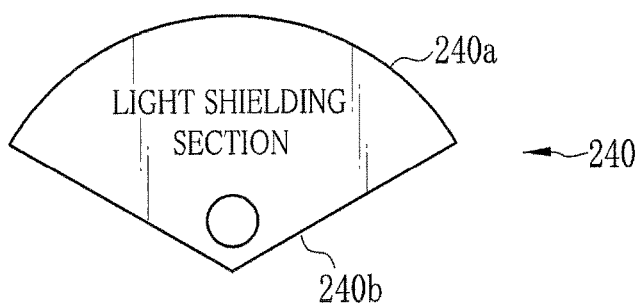
FIG. 25 is a plan view of a shutter plate.

As shown in FIG. 25, the shutter plate 240 includes a light shielding section 240*a* having a central angle of 120° for blocking the broad band light BB, and a light transmitting section 240*b* having a central angle of remaining 240° for transmitting the broad band light BB. The shutter plate 240 is rotatable. By the rotation of the shutter plate 240, the light shielding section 240*a* and the light transmitting section 240*b* are alternately and selectively inserted in the optical path of the broad band light BB.

The shutter plate 240 is rotatable between a position inserted in the optical path L1 of the broad band light BB and a position retracted from the optical path L1 of the broad band light BB. In the normal observation mode, the shutter plate 240 is stopped in such a state that the light shielding section 240*a* is retracted from the optical path L1 of the broad band light BB and the light transmitting section 240*b* is inserted into the optical path L1. Thus, the broad band light BB always enters the rotary filter 234. Accordingly, the three colors of light, i.e. the B light, the G light, and the R light are sequentially produced by the B, G, and R filters 234*a*, 234*b*, and 234*c* inserted in the optical path L1 of the broadband light BB.

Figure 26:
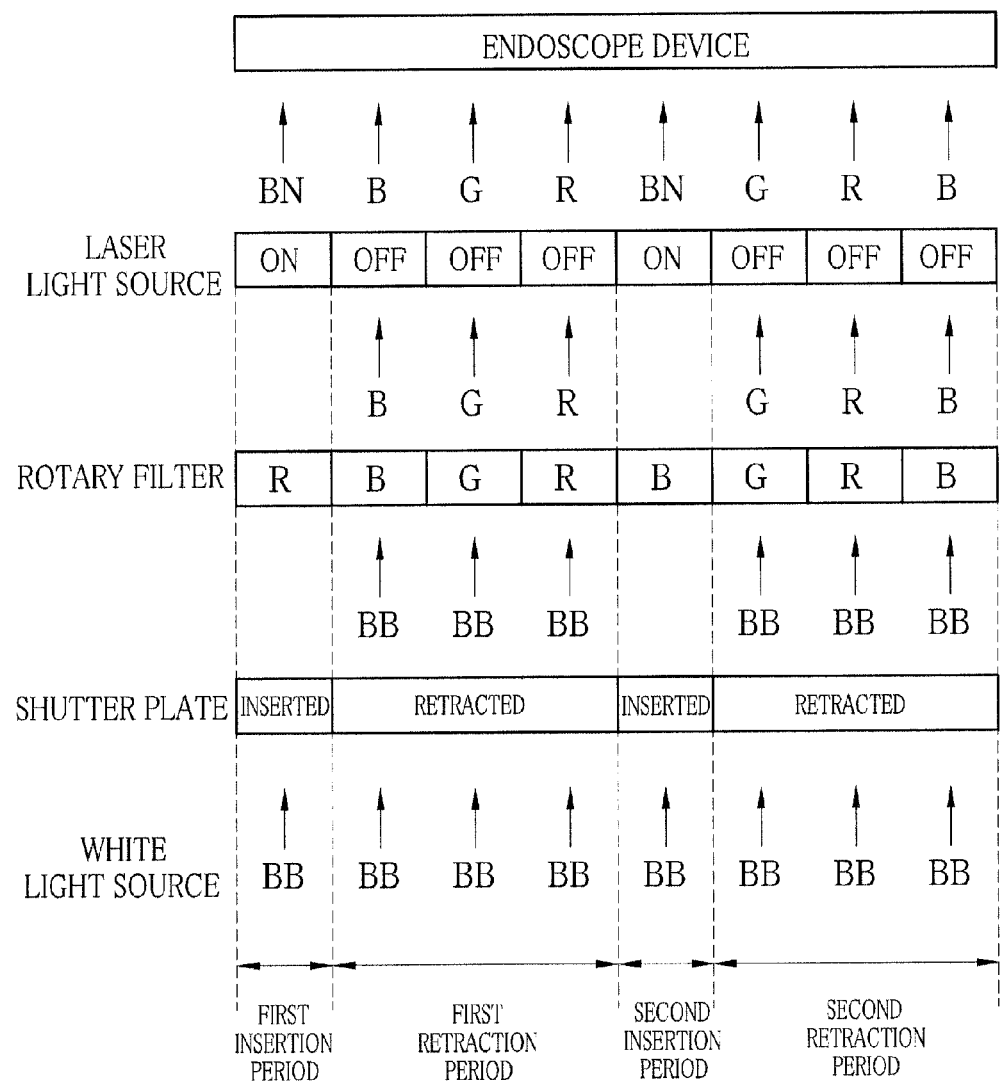
FIG. 26 is an explanatory view showing application timing of blue narrow band light BN, B light, G light, and R light to an endoscope device.

On the other hand, in the biological information observation mode, as shown in FIG. 26, the shutter plate 240 repeats intermittent operation between the inserted position and the retracted position. In an insertion period in which the shutter plate 240 is in the inserted position, the broad band light BB is not incident on the rotary filter 234, so the B light, the G light, and the R light from the rotary filter 234 is not supplied to the endoscope device 180. Instead of this, the laser light source 236*a* is turned on and the blue narrow band light BN is supplied to the endoscope device 180. This insertion period continues from the insertion of one color filter of the rotary filter 234 in the optical path L1 of the broad band light BB to the retraction of the one color filter therefrom, in other words, for a duration of a one-third turn of the rotary filter 234*a*.

After a lapse of the insertion period, the shutter plate 240 is rotated from the inserted position to the retracted position, to start a retraction period in which the shutter plate 240 is situated in the retracted position. This retraction period continues for a duration of one turn of the rotary filter 234. The three colors of light, i.e. the B light, the G light, and the R light are supplied to the endoscope device 180 in the retraction period.

Taking the case of FIG. 26 as an example, in a first insertion period in which the R filter 234*c* of the rotary filter 234 is inserted in the optical path L1 of the broad band light BB, the broad band light BB is not incident on the R filter 234*c*, and instead the blue narrow band light BN is supplied to the endoscope device 180. Then, upon starting a next first retraction period, the broad band light BB is sequentially incident on the B filter 234*a*, the G filter 234*b*, and the R filter 234*c*. Therefore, the B light, the G light, and the R light are supplied in this order to the endoscope device 180.

In a next second insertion period, the B filter 234*a* of the rotary filter 234 is inserted in the optical path L1, but the broad band light BB is not incident on the B filter 234*a*. The blue narrow band light BN is supplied to the endoscope device 180 in this second insertion period. Then, in a next second retraction period, the broad band light BB is sequentially incident on the G filter 234*b*, the R filter 234*c*, and the B filter 234*a* of the rotary filter 234, so the G light, the R light, and the B light are supplied in this order to the endoscope device 180.

The imaging device 180*a* of the endoscope device 180 is a monochrome imaging device having no micro color filter in its imaging surface, in contrast to the imaging device 60 of the above first and second embodiments. The imaging controller 70 for controlling the imaging operation of the imaging device 180*a* performs operation different from that in the above first and second embodiments.

Figure 27A:
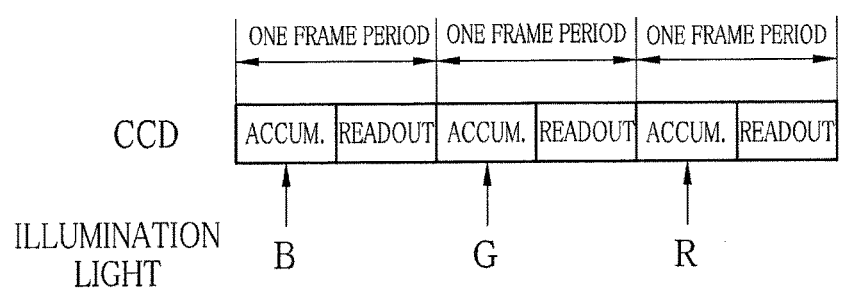
FIG. 27A is an explanatory view showing imaging control of the imaging device in the normal observation mode using the light source device of FIG. 22.
Figure 27B:
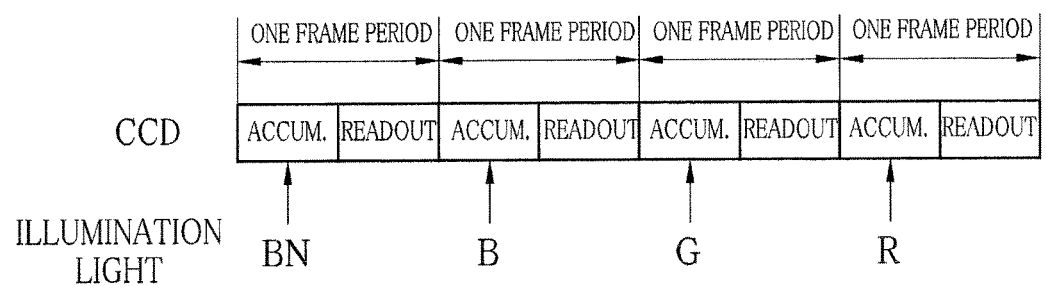
FIG. 27B is an explanatory view showing imaging control of the imaging device in the biological information observation mode using the light source device of FIG. 22.

In the normal observation mode, as shown in FIG. 27A, three colors of image light of B, G, and R is sequentially captured and electric charge is accumulated. Based on the accumulated electric charge, surface sequential imaging signals B, G, and R are sequentially outputted. This operation sequence is repeated during the normal observation mode. In the biological information observation mode, on the other hand, as shown in FIG. 27B, four types of image light, including the blue narrow band light BN, the B light, the G light, and the R light is sequentially captured and electric charge is accumulated. Based on the accumulated electric charge, surface sequential imaging signals N, B, G, and R are sequentially outputted. This operation is repeated during the biological information observation mode.

The normal light image processor 80 of the processor device 13 produces the normal light image based on the surface sequential imaging signals B, G, and R. In this normal light image, the surface sequential imaging signal B approximately corresponds to the blue signal B2 (Bc) of the first and second embodiments. The surface sequential imaging signal G approximately corresponds to the green signal G2 (Gc) of the first and second embodiments. The surface sequential imaging signal R approximately corresponds to the red signal R2 (Rc) of the first and second embodiments.

The function information image processor 82 of the processor device 13 calculates the blood volume and the oxygen saturation level based on the surface sequential imaging signals N, G, and R. N/G is used as a luminance ratio corresponding to the first luminance ratio B1/G2 of the first and second embodiments, and R/G is used as a luminance ratio corresponding to the second luminance ratio R2/G2 of the first and second embodiments. In accordance with it, the correlation memory 85 stores the correlation among the luminance ratios B1/G2 and R2/G2, the blood volume, and the oxygen saturation level. The same procedure as the first and second embodiments is performed as for the others.

Note that, the blood volume and the oxygen saturation level are imaged as the biological function information in the above first to fourth embodiments, but instead or in addition to this, an oxyhemoglobin index calculated by "blood volume (the sum of oxyhemoglobin and deoxyhemoglobin)×oxygen saturation level (%)" or a deoxyhemoglobin index calculated by "blood volume×(100-oxygen saturation level) (%)" may be imaged.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
   an image information obtaining section for obtaining image information by imaging an observation object;
   a biological function information calculating section for calculating biological function information of said observation object based on said image information;
   a first image generating section for producing a biological function information image that images said biological function information with artificial colors, said biological function information image composed of luminance information and color difference information;
   an emphasized image generating section for producing an emphasized image, in said emphasized image, a low reliability area which represents a calculation result of said biological function information calculating section has low reliability in said biological function information image because of too large luminance being further brightened for emphasis without changing color of said biological function information image, said emphasized image indicating reliability of said biological function information by brightness;

a second image generating section for producing based on said image information a normal light image that images said observation object irradiated with white light, wherein said emphasized image generating section produces said emphasized image by superimposing luminance of said normal light image on said biological function information image; and a display section for displaying said emphasized image, wherein said image information includes first image information, and second image information, said first image information being obtained by imaging said observation object under irradiation with first illumination light having a first wavelength range in which a light absorption coefficient varies with a variation in said oxygen saturation level, said second image information being obtained by imaging said observation object under irradiation with white light, wherein said biological function information calculating section calculates said biological function information based on said first image information and said second image information, and wherein said luminance information of said biological function information image is obtained from said second image information, and said color difference information of said biological function information image is obtained by inputting said biological function information into a color table previously stored in a memory.

2. The endoscope system according to claim 1, wherein said emphasized image generating section applies no information process to said color difference information of said biological function information image, and applies an information process to said luminance information of said biological function information image so as to further brighten said bright part within said abnormal area.

3. The endoscope system according to claim 1, wherein said emphasized image generating section adjusts a pixel value of said biological function information image so as to further brighten said bright part within said abnormal area.

4. The endoscope system according to claim 1 further comprising:
a halation detecting section for detecting whether or not a halation area exists in said biological function information image, in said halation area a pixel value exceeds a halation value being a certain value or more; and
a display control section for displaying said biological function information image on said display section in a case where said halation area is detected, and for displaying said emphasized image on said display section in a case where no halation area is detected.

5. The endoscope system according to claim 1, wherein said biological function information includes a blood volume being an amount of hemoglobin in blood and an oxygen saturation level of said hemoglobin in said blood.

6. The endoscope system according to claim 5, wherein said biological function information calculating section isolates information on said blood volume and information on said oxygen saturation level from a plurality of types of said biological function information included in said image information.

7. An operating method of an endoscope system comprising the steps of:
obtaining image information by an image information obtaining section by imaging an observation object;
calculating biological function information of said observation object based on said image information by a biological function information calculating section;
producing, by a first image generating section, a biological function information image that images said biological function information with artificial colors, said biological function information image composed of luminance information and color difference information;
producing an emphasized image by an emphasized image generating section, in said emphasized image, an abnormal area in which a calculation result of said biological function information calculating section is likely to be abnormal in said biological function information image because of too large luminance being further brightened for emphasis without changing color of said biological function information image, said emphasized image indicating reliability of said biological function information by brightness; and
displaying said emphasized image on a display section,
wherein said image information includes first image information and second image information, said first image information being obtained by imaging said observation object under irradiation with first illumination light having a first wavelength range in which a light absorption coefficient varies with a variation in said oxygen saturation level, said second image information being obtained by imaging said observation object under irradiation with white light,
wherein said biological function information is calculated based on said first image information and said second image information, and
wherein said luminance information of said biological function information image is obtained from said second image information, and said color difference information of said biological function information image is obtained by inputting said biological function information into a color table previously stored in a memory.

8. An endoscope system comprising:
an image information obtaining section for obtaining image information by imaging an observation object;
a biological function information calculating section for calculating biological function information of said observation object based on said image information;
a first image generating section for producing a biological function information image that images said biological function information with artificial colors, said biological function information image composed of luminance information and color difference information;
an emphasized image generating section for producing an emphasized image, in said emphasized image, a bright part within a low reliability area which represents a calculation result of said biological function information calculating section has low reliability n said biological function information image being further brightened for emphasis without changing color of said biological function information image, said emphasized image indicating reliability of said biological function information by brightness; and
a display section for displaying said emphasized image, wherein said emphasized image generating section produces said emphasized image in which luminance of said abnormal area is further increased by performing gain processing on said abnormal area having luminance more than a certain upper limit value in said emphasized image, wherein said image information includes first image information and second image information, said first image information being obtained by imaging said observation object under irradiation with first illumination light having a first wavelength range in which a light absorption coefficient varies with a variation in said oxygen saturation level, said second image information being obtained by imaging said observation object under irradiation with white light, wherein said biological function information calculating section calculates said biological function information based on said first image information and said second image information, and wherein said luminance information of said biological function information image is obtained from said second image information, and said color difference information of said biological function information image is obtained by inputting said biological function information into a color table previously stored in a memory.

9. The endoscope system of claim 1, further comprising:
a signal ratio calculator for calculating a ratio of intensity of each pixel between an image signal of a first frame period and an image signal of a second frame period,
wherein the biological function information image is produced based on the ratio of intensity of each pixel that is calculated.

* * * * *